US008305076B2

(12) United States Patent
Sack et al.

(10) Patent No.: US 8,305,076 B2
(45) Date of Patent: Nov. 6, 2012

(54) DEVICE AND METHOD FOR GENERATING MECHANICAL OSCILLATIONS IN AN EXAMINATION OBJECT USING MAGNETIC RESONANCE ELASTOGRAPHY

(75) Inventors: Ingolf Sack, Berlin (DE); Juergen Braun, Berlin (DE); Jens Rump, Berlin (DE); Jens Modrow, Berlin (DE)

(73) Assignee: Charite Universitatsmedizin Berlin, Berlin (DE)

( * ) Notice: Subject to any disclaimer, the term of this patent is extended or adjusted under 35 U.S.C. 154(b) by 678 days.

(21) Appl. No.: 12/297,133

(22) PCT Filed: Apr. 12, 2007

(86) PCT No.: PCT/EP2007/003417
§ 371 (c)(1),
(2), (4) Date: Feb. 27, 2009

(87) PCT Pub. No.: WO2007/118710
PCT Pub. Date: Oct. 25, 2007

(65) Prior Publication Data
US 2011/0006767 A1   Jan. 13, 2011

(30) Foreign Application Priority Data

Apr. 13, 2006 (DE) .......................... 10 2006 018 863
Apr. 13, 2006 (EP) ..................................... 06090057
Aug. 1, 2006 (DE) .......................... 10 2006 037 160

(51) Int. Cl.
*G01V 3/00* (2006.01)
(52) U.S. Cl. ..................................................... 324/309
(58) Field of Classification Search .......... 324/300–322; 600/410–435
See application file for complete search history.

(56) References Cited

U.S. PATENT DOCUMENTS

| 5,313,945 | A | 5/1994 | Friedlander |
| 5,524,636 | A | 6/1996 | Sarvazyan et al. |
| 5,810,731 | A | 9/1998 | Sarvazyan et al. |
| 5,899,858 | A * | 5/1999 | Muthupillai et al. ......... 600/410 |
| 6,037,774 | A | 3/2000 | Felmlee et al. |
| 6,246,895 | B1 | 6/2001 | Plewes |
| 6,486,669 | B1 | 11/2002 | Sinkus et al. |
| 6,647,134 | B1 | 11/2003 | McGee et al. |

(Continued)

FOREIGN PATENT DOCUMENTS

DE         29722630 U1      7/1998

(Continued)

OTHER PUBLICATIONS

Rump et al., "Synchronisation of shear vibrations and balanced steady state free precession in MR Elastography (SSFP-RRE)", In: Proc. Intl. Soc. Mag. Reson. Med., 2005, vol. 13, p. 2384.

(Continued)

*Primary Examiner* — Dixomara Vargas
(74) *Attorney, Agent, or Firm* — Rothwell, Figg, Ernst & Manbeck, P.C.

(57) ABSTRACT

A device and method for producing mechanical oscillations in a research object using magnetic resonance elastography (MRE) with a membrane that can be set into periodic motion and a transmission element for the transmission of periodic motion of the membrane onto the research object, whereby the membrane is connected to the transmission element by means of a mounting medium in such a way that periodic motion of the membrane is transmitted over the mounting medium to the transmission element.

22 Claims, 20 Drawing Sheets

U.S. PATENT DOCUMENTS

| | | | |
|---|---|---|---|
| 6,833,703 | B2 | 12/2004 | Sinkus et al. |
| 7,025,253 | B2 | 4/2006 | Sinkus et al. |
| 2002/0068870 | A1 | 6/2002 | Alam et al. |
| 2003/0065267 | A1 | 4/2003 | Smith |
| 2003/0236456 | A1 | 12/2003 | Graham et al. |
| 2004/0086969 | A1 | 5/2004 | Mary Lynne et al. |
| 2005/0065426 | A1 | 3/2005 | Porat et al. |
| 2005/0270029 | A1 | 12/2005 | Ehman et al. |

FOREIGN PATENT DOCUMENTS

| | | |
|---|---|---|
| DE | 199 36 554 C2 | 7/2003 |
| WO | 0070362 A1 | 11/2000 |
| WO | 03/073933 A1 | 9/2003 |
| WO | 2004/086969 A1 | 10/2004 |
| WO | 2004/091408 A2 | 10/2004 |
| WO | 2005/120344 A1 | 12/2005 |

OTHER PUBLICATIONS

Papazoglou et al., "Two-Dimensional Waveform Analysis in MR Elastography of Skeletal Muscles", Phys. Med. Biol., 50(2005) 1313-1325.
Muthupillai et al., "Magnetic Resonance Elastography by Direct Visualization of Propagating Acoustic Strain Waves", Science, vol. 269, pp. 1853-1857.
Othman et al, "Microscopic Magnetic Resonance Elastography (μMRE)", Magnetic Resonance in Medicine, 54:605-615 (2005).
Overall et al., "Fast Phase-Contrast Velocity Measurement in the Steady State", Magnetic Resonance in Medicine, 48:890-898(2002).
Zur et al., "Motion-Insensitive, Steady-State Free Precession Imaging", Magnetic Resonance in Medicine, 16, 444-459 (1990).
Sack et al., "Observation of Nonlinear Shear Wave Propagation Using Magnetic Resonance Elastography", Magnetic Resonance in Medicine, 52:842-850 (2004).
Sinkus et al., "High-Resolution Tensor MR elastography for breast tumour detection", Phys.Med. Biol., 45(2000) 1649-1664.
Sinkus et al., "Imaging Anisotropic and Viscous Properties of Breast Tissue by Magnetic Resonance-Elastography", Magnetic Resonance in Medicine, 53:372-387(2005).
Van Houten et al., "An Overlapping Subzone Technique for MR-Based Elastic Property Reconstruction", Magnetic Resonance in Medicine 42: 779-786 (1999).
Weaver et al., "Magnetic Resonance Elastography using 3D Gradient Echo Measurements of Steady-State Motion", Med. Phys. 28 (8), Aug. 2001, 1620-1628.
Park et al., "Rapid Measurement of Time-Averaged Blood Flow Using Ungated Spiral Phase-Contrast", Magnetic Resonance in Medicine 49:322-328 (2003).
Patz, "Some Factors that Influence the Steady State in Steady-State Free Precession", Magnetic Resonance Imaging, vol. 6, pp. 405-413, 1988.
Romano et al., "Determination and Analysis of Guided Wave Propagation using Magnetic Resonance Elastography", Magnetic Rsonance in Medicine 54:893-900 (2005).
Lewa et al., "Viscoelastic Property Detection by Elastic Displacement NMR Measurements" , JMRI 1996: 6: 652-656.
Papazoglou et al., "Group-Velocity Inversion in MR Elastography on Skeletal Muscles", Pro. Intl. Soc. Mag. Reson. Med., 14 (2006), p. 2557.
Wen et al, "Magnetic Resonance Imaging Assessment of Myocardial Elastic Modulus and Viscosity Using Displacement Imaging and Phase-Contrast Velocity Mapping", Magnetic Resonance in Medicine, 54:538-548 (2005).
Bieri et al, "Balanced Alternating Steady-State Elastography", Magnetic Resonance in Medicine 55: 233-241 (2006).
Chenevert et al., "Elasticity Reconstructive Imaging by Means of Stimulated Echo MRI", MRM, 39:482-490 (1998).
Grinstead et al., "In-Plane Velocity Encoding with Coherent Steady-State Imaging", Magnetic Resonance in Medicine, 54: 138-145 (2005).
Gyngell, "The Application of Steady-State Free Precession in Rapid 2DFT NMR Imaging: Fast and CE-Fast Sequences", Magnetic Resonance Imaging, vol. 6, pp. 415-419, 1988.
McCracken et al., "Mechanical Transient-Based Magnetic Resonance Elastography", Magnetic Resonance in Medicine 53:628-639 (2005).
Oppelt et al., "FISP: A New Fast Pulse Sequence for Magnetic Resonance Tomography", Electromedica 54 (1986), 15-18, with English Abstract.
Fung, Mechanical Properties of Living Tissues, Biomechanics, pp. 10-23, 1993.
Rump et al, Desynchronized Motion Encloding in Rapid Steady-State Free Precission MR Elastography, Abstract ISMRM 2006 (8—Dec. 5, 2006).
Bernstein et al., "Handbook of MRI Pulse Squences", Chapter 15, Angiographic Pulse Squences, pp. 658-679.
Sarvazyan et al., Biophysical Bases of Elasticity Imaging, Acoustical Imaging (ed. J.P. Jones), vol. 21, 1995, pp. 1-17.
Scheffler et al., "A Pictorial Description of Steady-States in Rapid Magnetic Resonance Imaging", Concepts in Magnetic Resonance, vol. 11(5), 291-304 (1999).
Bernstein et al., "Comparison of Phase-Difference and Complex-Difference Processing in Phase-Contrast MR Angiography", JMRI, 1991; 1: pp. 725-729.
Bieri et al., "Flow Compensation in Balanced SSFP Sequences", Magnetic Resonance in Medicine, 54; pp. 901-907 (2005).
Braun et al., "In Vivo Magnetic Resonance Elastography of the Human Brain Using Ultrafast Acquisition Techniques", Pro. Intl. Soc. Mag. Reson. Med. 10, (2002).
Braun et al., "Electromagnetic Actuator for Generating Variably Oriented Shear Waves in MR Elastography", Magnetic Resonance in Medicine, 50: pp. 220-222 (2003).
Carr, "Steady-State Free Precession in Nuclear Magnetic Resonance", Physical Review, vol. 112, No. 5, Dec. 1, 1958, pp. 1693-1708.
Catheline et al., "A solution to diffraction biases in sonoelasticity: The acoustic impulse technique", J. Acoust. Soc. Am., 105 (5), May 1999, pp. 2941-2950.
Catheline et al., "Measurement of viscoelastic properties of homogeneous soft solid using transient elastography: An inverse problem approach", J. Acoust. Soc. Am., 116 (6), Dec. 2004, pp. 3734-3741.
Grimm et al., "Improved Phase to Noise Ratio for Short T2* Spins in MRE", Proc. Intl. Soc. Mag. Reson. Med., 11 (2004), p. 572.
Hargreaves et al.,"Characterization and Reduction of the Transient Response in Steady-State MR Imaging", Magnetic Resonance in Medicine, 46: 149-158 (2001).
Kanai et al., "Propagation of Spontaneously Actuated Pulsive Vibration in Human Heart Wall and in Vivo Viscoelasticity Estimation", IEEE Transactions on Ultrasonics, Ferroelectrics, and Frequence Control, vol. 52, No. 11, Nov. 2005, pp. 1931-1942.
Klatt et al., "In Vivo Determination of Hepatic Stiffness Using Steady-State Free Precession Magnetic Resonance Elastography", Investigative Radiology, vol. 41, No. 12, Dec. 2006, pp. 841-848.
Kruse et al., "Palpation of the Brain" Using Magnetic Resonance Elastography, 2000.
Lemke et al., "Living Donor Right Liver Lobes: Preoperative CT Volumetric Measurement for Calculation of Intraoperative Weight and Volume", Radiology, vol. 240, No. 3, Sep. 2006, pp. 736-742.
Lerner et al., "Sonoelasticity Images Derived from Ultrasound Signals in Mechanically Vibrated Tissues", Ultrasound in Med & Biol., vol. 16, No. 3, pp. 231-239, 1990.
Markl et al., "Balanced Phase-Contrast Steady-State Free Precession (PC-SSFP): A Novel Technique for Velocity Encoding by Gradient Inversion", Magnetic Resonance in Medicine, 49:945-952 (2003).
Oliphant et al., "Complex-Valued Stiffness Reconstruction for Magnetic Resonance Elastography by Algebraic Inversion of the Differential Equation", Magnetic Resonance in Medicine, 45:299-310, (2001).
Ophir et al., "Elastography: A Quantitative Method for Imaging the Elasticity of Biological Tissues", Ultrasonic Imaging, 13, p. 111-134 (1991).
Papazoglou et al., "Shear Wave Group Velocity Inversion in MR Elastography of Human Skeletal Muscle", Magnetic Resonancne in Medicine, 56: 489-497 (2006).
Pelc et al., "Encoding Strategies for Three-Direction Phase-Contrast MR Imaging of Flow", JMRI, 1991: 1, 405-413.

Plewes et al., "Visualizing Tissue Compliance with MR Imaging", JMRI, 1995: 5: 733-738.

Plewes et al., "Magnetic Resonance Imaging of Ultrasound Fields: Gradient Characteristics", Journal of Magnetic Resonance Imaging, 11:452-457 (2000).

Rump et al., "Fractional Encoding of Harmonic Motions in MR Elastography", Magnetic Resonance in Medicine, 57:388-395 (2007).

Scheffler et al., "Principles and applications of balanced SSFP techniques", EUR Radiol, (2003), 13: 2409-2418.

Sack et al., "Analysis of wave patterns in MR elastography of skeletal muscle using coupled harmonic oscillator simulations", Magnetic Resonance Imaging 20 (2002), pp. 95-104.

Weaver et al., "Encoding Harmonic Motion in MR Elastography using the Imaging Gradients", Proc. Intl. Soc. Mag. Reson. Med., vol. 11 (2003), p. 1077.

Wood et al., "MR image artifacts from periodic motion", Med. Phys. 12(2), Mar./Apr. 1985, pp. 143-151.

\* cited by examiner

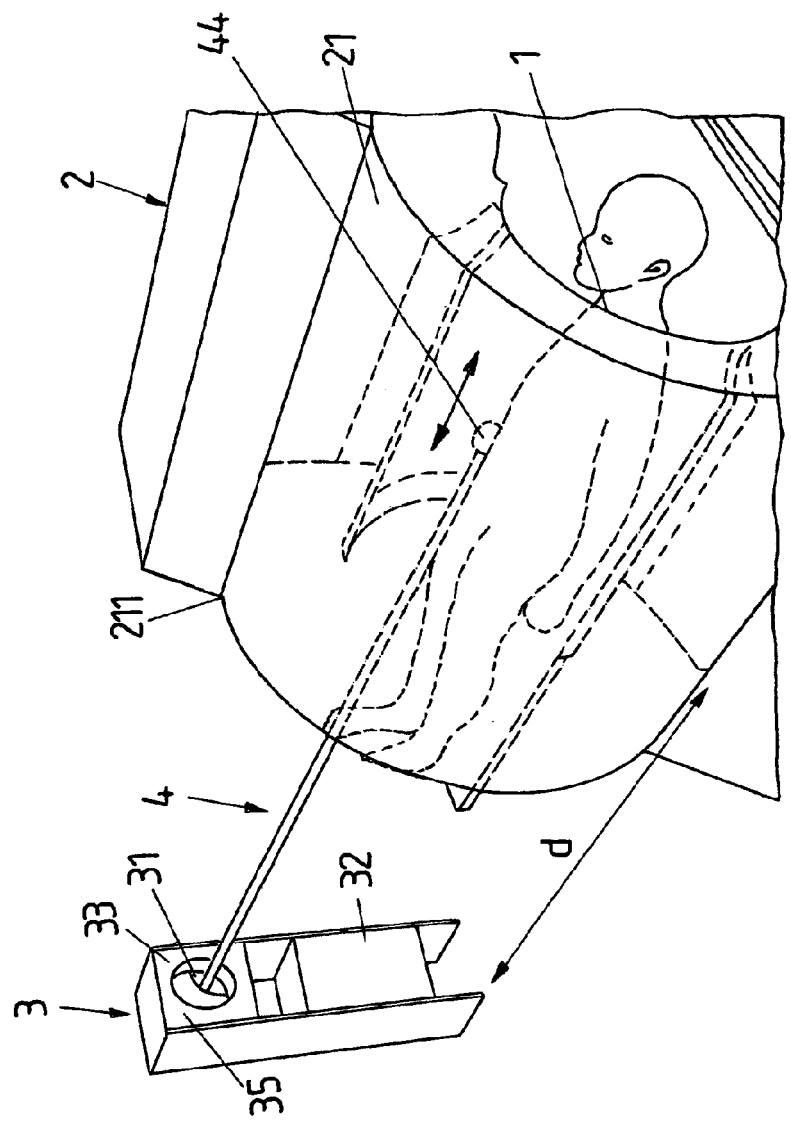

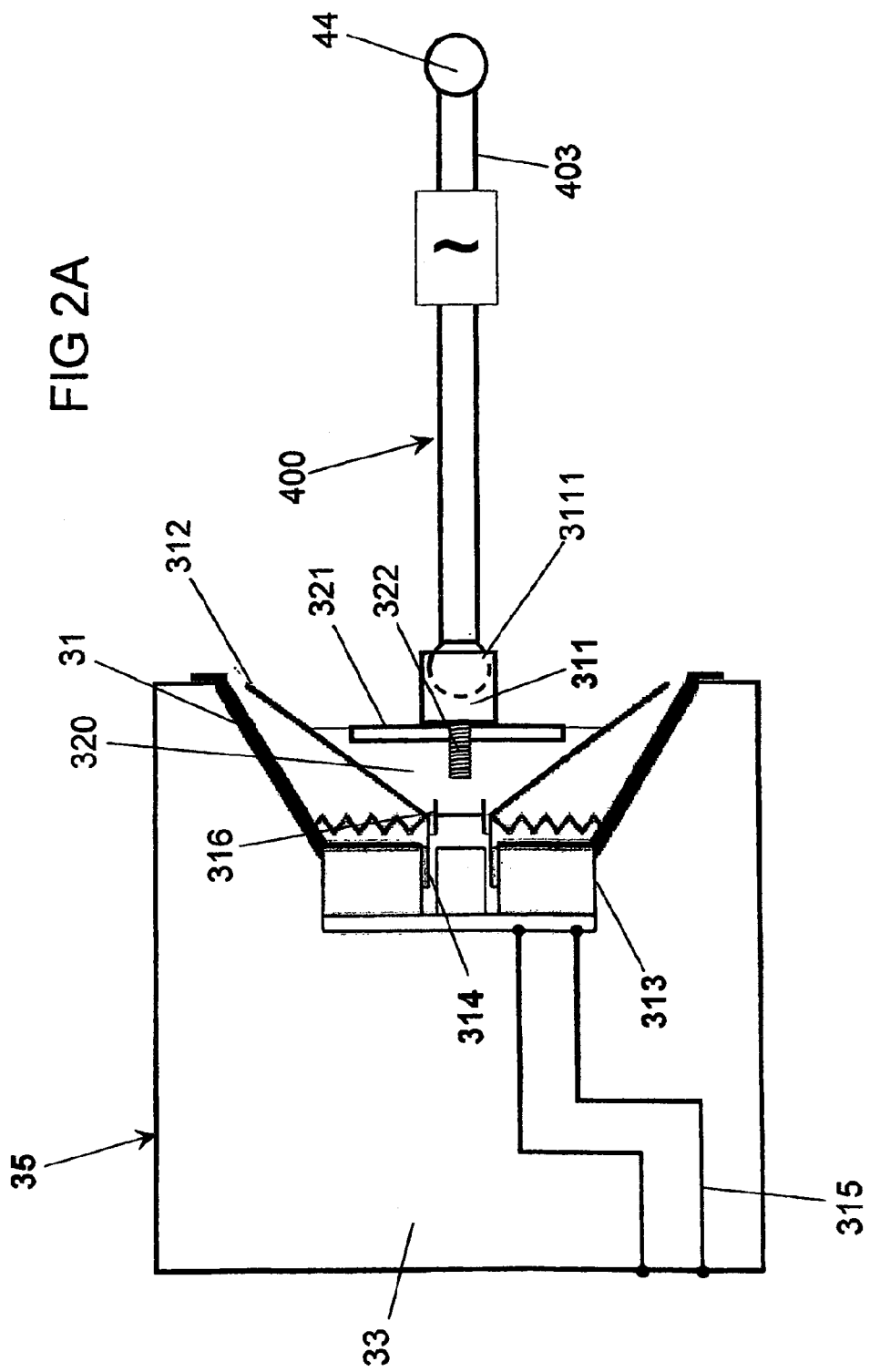

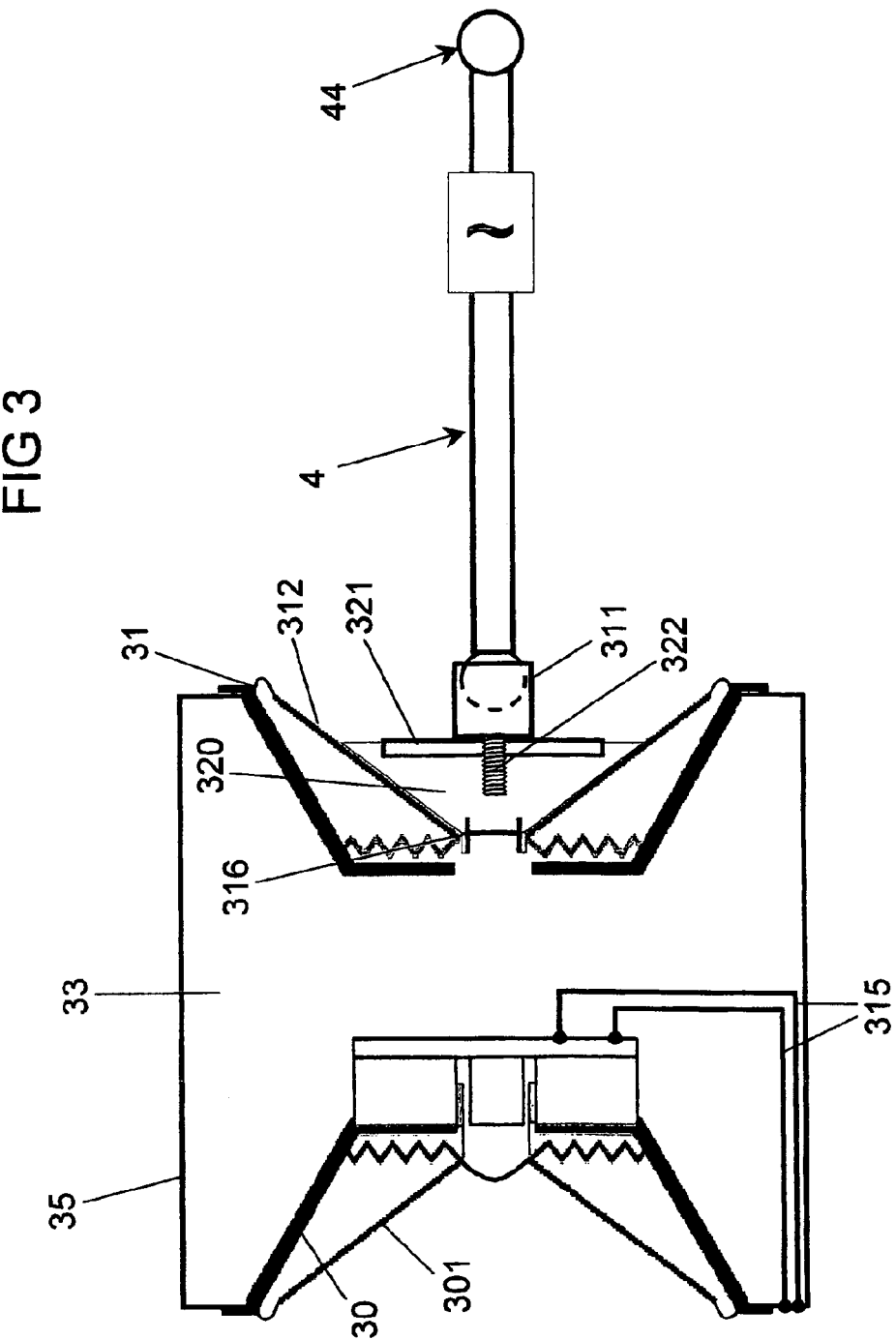

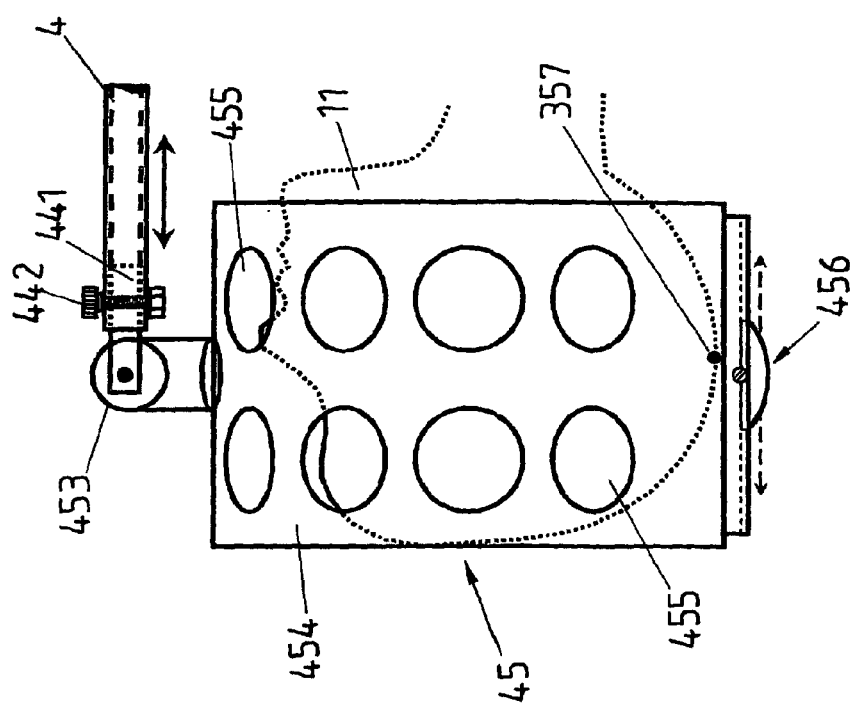

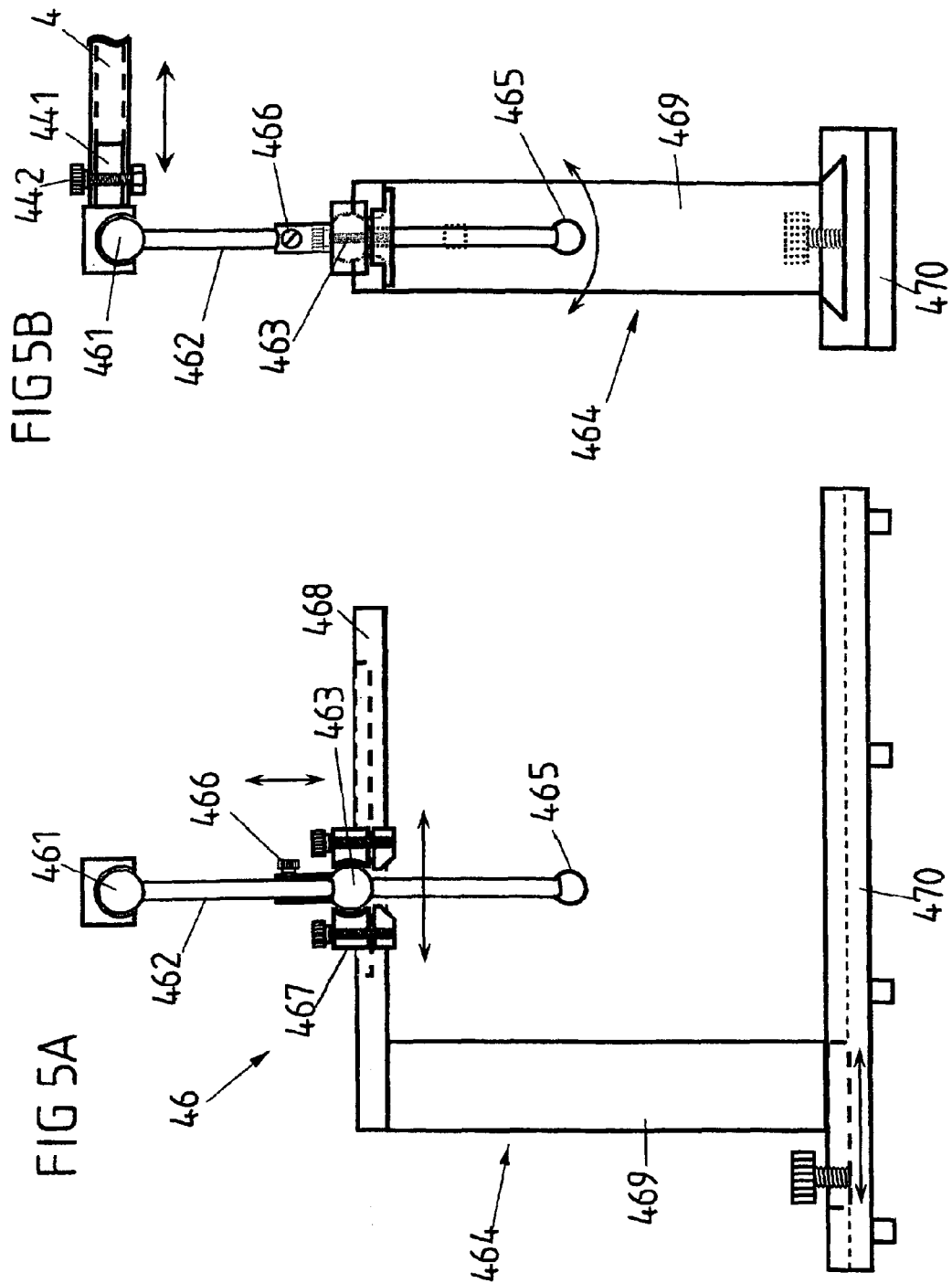

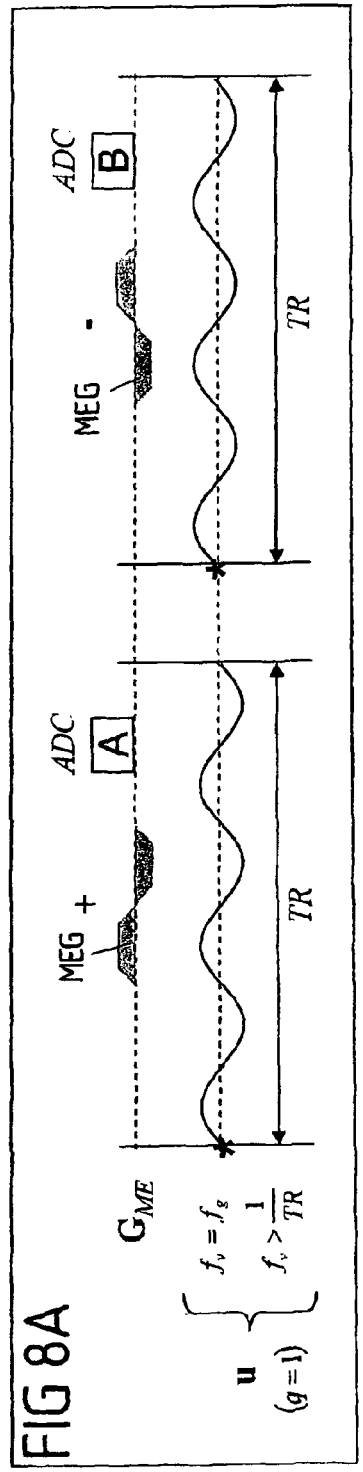
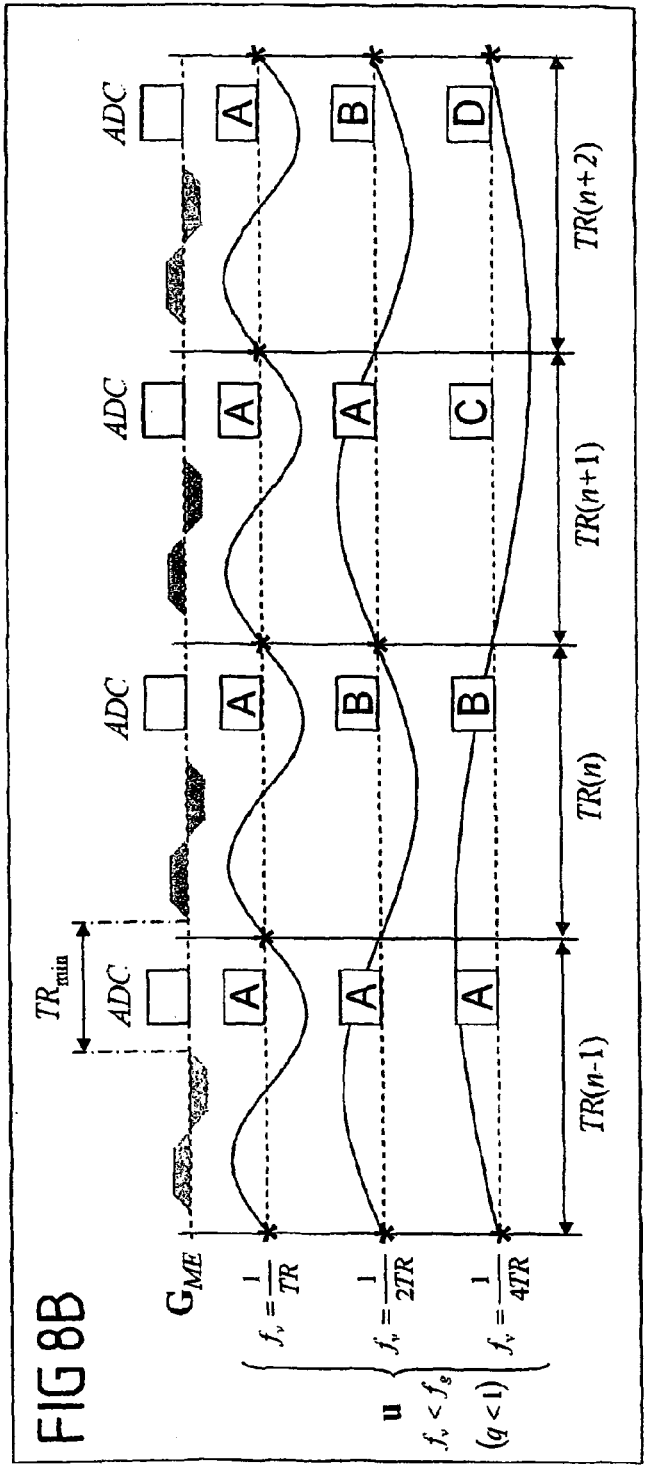

Fig 17

| tissue | $n_v$ | $f_v$ [Hz] | $f_g$ [Hz] | result of a single scan (cf. fig.1) | total scan time * | PNR | $\mu$ [kPa] |
|---|---|---|---|---|---|---|---|
| skeletal muscle (biceps) | 1 | 120 | 200 | $\varphi(\theta) = A$ or $B$ | 50 sec | 3.6 | 5.7 ± 0.9 (perpendicular)<br>30.9 ± 5.2 (parallel) |
| liver | ½ | 50 | 150 | $\Delta\varphi(\theta) = A - B$ | 4 breath-holds | 0.7 | 2.7 ± 0.5 |
| myocardium (IVS) | ¼ | 50 | 500 | $\Delta\varphi(\theta) = A - C$<br>$\Delta\varphi(\theta + 90°) = B - D$ | 64 heart cycles ** | 0.4 | 24 – 30 #<br>0.5 – 1.2 ## |

DEVICE AND METHOD FOR GENERATING MECHANICAL OSCILLATIONS IN AN EXAMINATION OBJECT USING MAGNETIC RESONANCE ELASTOGRAPHY

CROSS REFERENCE TO RELATED APPLICATION

This application is a 35 U.S.C. 371 National Phase Entry Application from PCT/EP2007/003417, filed Apr. 12, 2007, which claims the benefit of German Patent Application No. 10 2006 018 863.2 filed on Apr. 13, 2006 in the German Intellectual Property Office, European Patent Application No. 06090057.8 filed Apr. 13, 2006 in the European Intellectual Property Office and German Patent Application No. 10 2006 037 160.7 filed on Aug. 1, 2006 in the German Intellectual Property Office, the disclosures of which are incorporated herein in their entirety by reference.

BACKGROUND OF THE INVENTION

This invention relates to a device for generating mechanical oscillations in an examination object using magnetic resonance elastography (MRE) according to the generic part of claim 1 and to a process for the magnetic resonant elastographic determination of biomechanical properties of tissue according to claim 23.

By means of magnetic resonance elastography (MRE) it is possible to detect biomechanical properties of biological tissues. This method is comparable with "instrumental palpatory findings", with which it is possible, however, to quantify the biomechanical properties not only of subsurface, but also of deep-seated tissues or organs with good transillumination and resolution. Comparable to classical palpation, but without limitation to subsurface tissues and objectively measurable, information on pathological changes of tissues and organs thus is accessible. MRE is based on the principles of magnetic resonance tomography (MRT). In the case of MRE, however, periodic particle displacements in the tissue to be examined must be generated in addition by means of mechanical excitation. The detection of particle motion, however, is effected by magnetic preparation of the nuclear spins and by motion-sensitive phase contrast techniques.

The resulting gray-scale images have a typical wave character, which represents the periodic tissue distortions (shear waves) caused by the mechanical excitation. From the distortions detected, elastic characteristics of the tissue such as shear modulus, Young's modulus, compression modulus or Poisson ratio can be calculated. Measuring the distortion in all spatial directions allows the complete quantification of the elastic characteristics in consideration of their directional dependence.

Examinations of the frequency and amplitude dependence of the periodic tissue distortions thus provide information on viscoelastic properties of tissues. Non-linear stress-distortion relationships, which likewise have a high potential for characterizing tissue properties, are accessible by measuring harmonic oscillations of the tissue distortion, which are present along with the excitation frequency.

The number of observable shear waves in the tissue to be examined depends on the elastic properties thereof and on the frequency of the mechanical excitation. So far, three different types of mechanical excitation units have been used in MRE, in order to generate displacements in tissues, including:
1) excitation units which are based on the linear expansion of piezoelectric crystals,
2) excitation units which are based on a motion reversal of current-carrying coils moving in the magnetic field of the tomograph (electromechanical excitation),
3) passive, pressure-activated excitation units which are driven via pneumatic lines.

The known devices have a number of limitations and disadvantages in connection with the previously available excitation methods. For instance:
1) Piezoelectric methods:
   High voltage: Piezoelectric crystals are operated with high-voltage amplifiers with a voltage of up to 1 kV. This is problematic for use in patient examinations and involves an enormous safety effort.
   Complex mechanics: Since the displacement amplitudes also of piezostacks with a length of 200 mm lie in the range of 200 µm, reversals must be realized by means of levers, in order to provide for displacements in the order of 1 mm.
   Phantom images: Due to lever reversal, springs, and an aluminum sleeve with a length of about 250 mm, in which the piezocrystals are biased, problems arise in connection with phantom images. The same are caused by the various metal parts necessary for construction, which lead to distortions of the magnetic field and hence to phantom images, the extent of which partly renders the evaluation of the image material impossible.
   Positioning: Due to the length of the finished excitation unit of usually 250 mm and a maximum diameter of the tomograph of 60 cm, positioning the excitation unit in part only is possible to a restricted extent depending on the examination object.
2) Electromechanical excitation units:
   Positionability: The main disadvantage of the electromechanical excitation units is the limitation to specified coil orientations in the magnetic field, as otherwise the magnetic fields necessary for the motion cannot be induced by the alternating voltage applied. As a result, applicability either is restricted or complicated mechanical reversal mechanisms become necessary.
   Phantom images: The use of aluminum for an improved dissipation of heat and enameled copper wire in turn leads to image extinctions, for whose prevention the coil of the mechanical excitation unit must be located at least 2 coil diameters away from the examination object. The magnetic fields induced therein additionally cause phantom images in dependence on the alternating voltage increasing with the displacement. This often prevents the generation of larger displacement amplitudes advantageous for MRE image material to be evaluated reliably.
   Phantom images caused by power supply cables: For the power and voltage supply of electromechanical excitation units, corresponding cables are required, which reach into the center of the magnet of the tomograph. Although shielded cables are used, which lead over a filter plate into the examination room, electromagnetic interferences, which are trapped by the cables and in turn lead to image artifacts, cannot always be excluded.
   For the different organs/tissues to be examined special excitation units must be developed, which are optimally adapted to the respective requirements.

In MRE, the mechanical tissue oscillations (shear waves) induced are detected by means of magnetic resonance tomography (MRT). For this purpose, the motions of the particles in the tissue must be encoded magnetically, which according to the prior art is effected by means of synchronously oscillating magnetic field gradients, i.e. the acoustic excitation for generating the oscillations and the magnetic encoding are effected with identical frequencies.

Oscillating motion encoding gradients (MEG) can be included in almost any MRT imaging technique. Therefore, MRE imaging techniques now are available, which are based on the principles of spin-echo or gradient-echo techniques. Particularly interesting imaging techniques include fast EPI (echo planar imaging) or SSFP (steady-state free precession) imaging techniques.

BRIEF SUMMARY OF THE INVENTION

It is the object underlying the present invention to create a possibility for performing MRE examinations more efficiently than in the past.

This object is solved by the device with the features according to claim 1 and by the method with the features according to claim 23. Preferred and particularly advantageous developments of the invention are indicated in the sub-claims.

Accordingly, there is provided a device for generating mechanical oscillations in an examination object for magnetic resonance elastography (MRE). The device includes: a membrane which can be set into periodic motions and a transmission element for transmitting periodic motions of the membrane onto the examination object. The membrane is connected with the transmission element via mounting means such that periodic motions of the membrane are passed on to the transmission element via the mounting means, in order to generate mechanical oscillations in the examination object.

Coupling of the membrane motions thus is effected directly via the mechanical connection of membrane and transmission element and not via a gaseous medium present between the membrane and the transmission element. Accordingly, the membrane oscillations are transmitted onto the transmission element not via pressure fluctuations (e.g. of an air-filled cavity), but directly via the mounting means for mounting the transmission element to the membrane.

The present invention is an acousto-mechanical excitation unit for MRE, which provides for a trouble-free, direct and exactly localizable transmission of vibrations with high performance into any body tissues or organs. There are no interactions with the electronics or the receiving components of a magnetic resonance tomograph for the detection of tissue oscillations.

BRIEF DESCRIPTION OF THE SEVERAL VIEWS OF THE DRAWINGS

FIG. 1B shows a three-dimensional representation of an MRE system;

FIG. 2A shows a detailed view of a first variant of the oscillation generating device;

FIG. 3 shows a third variant of the oscillation generating device;

FIG. 4 shows a side view of an end piece of a transmission element for generating shear waves in the brain;

FIG. 5A, 5B show side and front views of a variable end piece of a transmission element;

FIG. 8A, 8B show the fundamental time course of mechanical excitation and motion encoding in MRE;

FIG. 17 lists representative parameters of the in vivo fractional MRE on biceps, liver and IVS.

DETAILED DESCRIPTION OF THE INVENTION

Figure 1A:
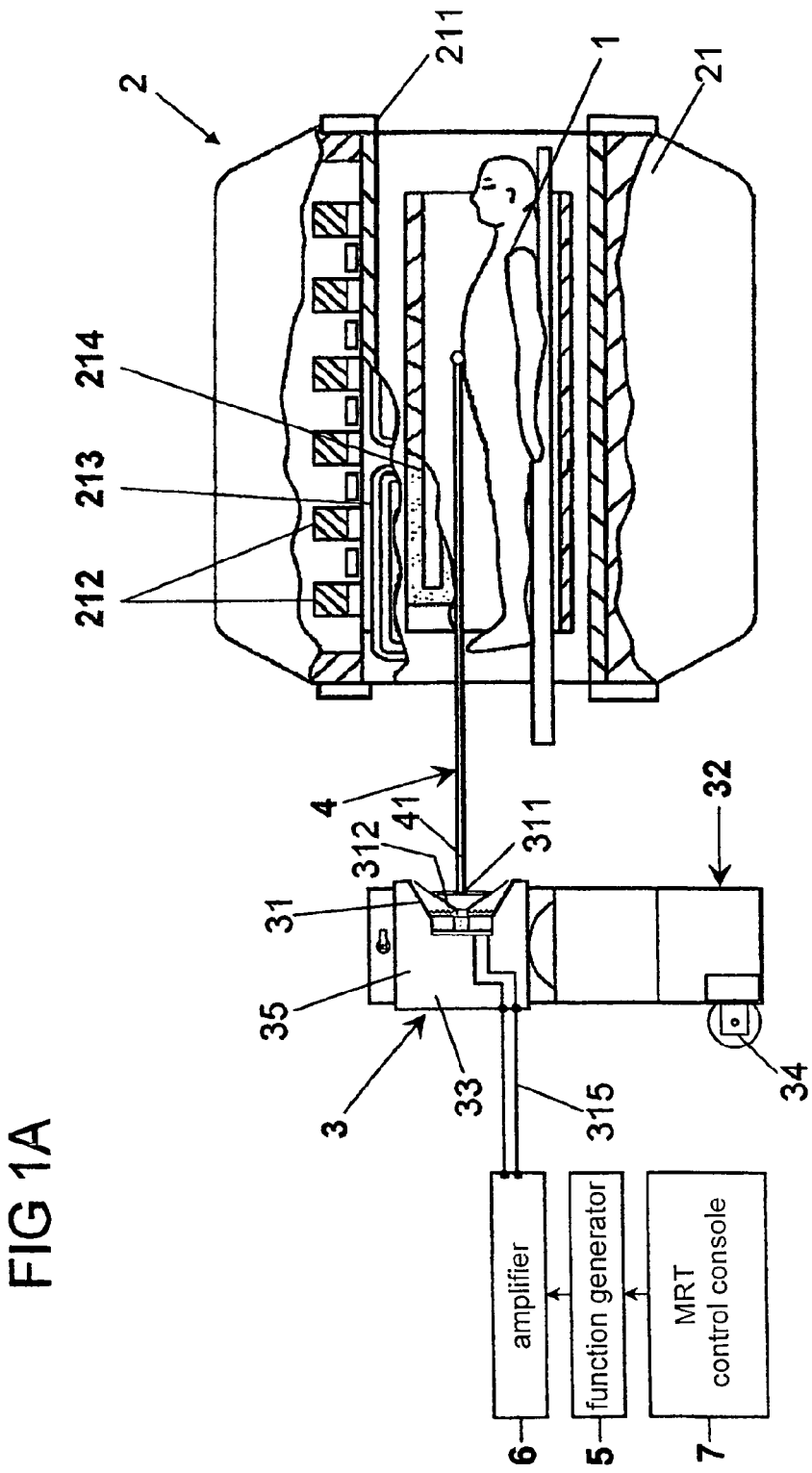
FIG. 1A shows a side view of an MRE system with an oscillation generating device.

In principle, any kind of mounting means can be used, as far as they on the one hand ensure a stable connection between the membrane and the transmission element and on the other hand forward the membrane oscillations to the transmission element (with as little attenuation as possible). For this purpose, e.g. elements for producing a screw or rivet connection can be used.

In a preferred variant, the mounting means include a supporting plate connected with the transmission element, which is centrally attached to the membrane by means of an adhesive.

As compared to the use of piezoelectric, electromechanical and pneumatic excitation units, the device in accordance with the invention provides for instance the following advantages:

No high-voltage technique; expensive measures for protecting patients and staff against dangerous high voltage can be omitted.

No phantom images due to moving or stationary metallic components inside or in the vicinity of the MR detection coil and the magnet of the MR tomograph.

No phantom images caused by induced additional magnetic fields.

Unlimited frequency range for mechanical excitation in MRE applications.

Efficient and exactly localizable power transmission.

Increased patient comfort and easier handling, as different positions selectively are excited depending on the application and no complete excitation units must be fixed at the body.

In a further, preferred aspect of the device in accordance with the invention, a surface of the membrane is connected with the transmission element, e.g. that surface of the membrane which points in the direction of the examination object. In particular, the connection can be made by bonding, e.g. by means of an adhesive. Particularly advantageously, a tubular or rod-shaped transmission element is used, one end of which is coupled to the membrane surface. The transmission element can extend linearly; however, it can also have a curved shape. It is decisive that the transmission element induces an oscillation sufficient for MRE in the examination object (person or tissue sample).

The transmission element can be e.g. a solid, rigid rod or a tube (rigid or flexible). Furthermore, a tube filled with a medium (gas or liquid) can also be provided. Such filled tube is connected for instance with the membrane surface in a gas- or liquid-tight way, so that the membrane motions are transmitted directly to the gas or liquid and passed on to the examination object.

Particularly preferably, the end of the transmission element is connected with a central portion of the membrane. When using a round membrane (e.g. a loudspeaker membrane), the end of the tubular or rod-shaped transmission element is connected with the membrane in the center thereof. Here, the membrane can additionally include a centrally arranged stabilizing sleeve for power transmission. In addition, a joint can be provided, which on one side is connected with the transmission element and on the other side with the membrane, possibly via the stabilizing sleeve.

In an advantageous development of the invention, the transmission element is flexible. In particular, a flexible transmission element can have a curved shape. In this connection, flexible does not necessarily mean "elastic". In any case, the material of the transmission element is chosen such that the membrane oscillations are passed on with as little attenuation as possible.

Particularly advantageously, a second membrane is arranged beside the first membrane connected with the transmission element and the first membrane can be set in motion by motions of the second membrane. Here, the second membrane constitutes an active membrane, and the first one is a passive membrane. Between the two membranes, an air-filled cavity can be provided, via which motions of the active membrane are transmitted to the passive membrane; for instance, the two membranes can be mounted on opposite side walls of a common housing which includes the air-filled cavity.

Furthermore, it is advantageously provided that on its side facing the examination object the transmission element includes a tubular or rod-shaped excitation element extending at an angle with respect to its main direction of extension. This provides for an efficient coupling into the examination object (e.g. a person in lying position). "Main direction of extension" is understood to be the extension of the transmission element in a direction from the membrane to the examination object. In a rod-shaped transmission element, its end not connected with the membrane is bent towards the examination object, for instance by means of a joint.

Carbon tubes, carbon rods or rigid connections which can be made by solid materials represent a possibility for the direct power transmission free of compression. This concept can also be realized by employing hydraulic apparatuses by using all suitable incompressible or slightly compressible fluids. Power transmission here is generally based on the transmission of a periodic force by a hydraulic fluid (for instance by means of a hydraulic piston) to an expandable membrane connected by means of a non-elastic and non-magnetic pressure tube. This membrane can be made of all expandable materials such as elastomers, rubber and plastics.

The method in accordance with the invention for the magnetic resonant elastographic determination of biomechanical properties of tissue includes the following steps:

a) inducing mechanical oscillations with a frequency $f_v$ in the tissue to be examined;
b) detecting the mechanical oscillations in the tissue by means of magnetic resonance, wherein a periodic magnetic field with a repeat time $TR \leq 1/f_v$ is applied to the tissue.

As already described above, MRE on the one hand comprises inducing mechanical oscillations in the tissue to be examined and on the other hand detecting these oscillations by a magnetic resonance method. Via characteristics (e.g. wavelength) of oscillations detected by means of the magnetic resonance method in the tissue (shear waves), biomechanical properties of the tissue can then be determined (elastic modulus, viscosity).

The periodic magnetic field used in connection with magnetic resonance for detecting the oscillations in the tissue advantageously is an MRE sequence, which includes subsequences repeated with the repeat time TR. The repetitive MRE subsequences thus represent the periodic magnetic field which is applied to the tissue.

As already mentioned above, an MRE sequence comprises an imaging sequence of the conventional MRT (MRT sequence). Such MRT sequence usually includes a radio signal (RF signal) for displacing the spin and pulse-like magnetic fields of different duration for preparation of the spins. The radio signal and the magnetic fields are repeated correspondingly with the repeat time TR of the MRT sequence.

By means of magnetic resonance, an image (i.e. a pictorial representation) of the tissue and of the oscillations induced in the tissue can be generated. Generating such image requires one or more imaging steps, wherein each imaging step comprises applying an MRE subsequence and thus a time period which corresponds to the repeat time TR of the MRE subsequence.

An image can be composed of one image line or of a plurality of image lines, wherein one image line or a plurality of image lines of the image are generated with one MRE sequence. It should be noted that generating an image can also be effected by means of an MRE sequence which includes no periodic subsequences (but only one single MRE sequence).

The magnetic resonance method for detecting oscillations thus is based on a conventional MRT method and in addition to the usual MRT magnetic field sequence comprises a magnetic field sequence (motion encoding sequence) for encoding (i.e. for "visualizing") the tissue oscillations. The combination of an MRT sequence and a motion encoding sequence represents the MRE sequence. The motion encoding sequence can for instance be a time-dependent gradient field (MEG). As mentioned already, any kind of MRT method (in which the motion encoding sequence is embedded) can be used in principle and is chosen with regard to the desired application, e.g. an EPI or SSFP method. MRT methods, however, are known per se, so that they will not be described here in detail.

For the MRT method of the invention it is decisive that the repeat time TR of the periodic magnetic field (e.g. of the MRE subsequences) is smaller than or equal to the inverse of the excitation frequency $f_v$ for generating mechanical oscillations in the tissue.

In conventional MRE, the excitation frequency for the tissue oscillations $f_v$ is identical with the frequency $f_g$ of the motion encoding sequence for encoding the oscillations (e.g. the MEG frequency in the case of a gradient field). In conventional MRE, the repeat time TR therefore always is greater than $1/f_v$. As compared to conventional MRE, the MRE method of the invention (with $TR \leq 1/f_v$) offers two decisive advantages:

1) reduction of the encoding time, i.e. acceleration of MRE images
2) reduction of the excitation frequency and hence increase of the penetration depth of the shear waves and of the effective phase signal for soft and viscous materials, respectively.

Item 1) allows the use of fast steady-state imaging techniques (SSFP) with a TR in the range of 5 ms. Hence, MRE images with an SSFP-typical good SNR (signal-to-noise ratio) can be taken within less than one second. At the same time, item 2) provides for an excellent illumination of the tissue to be examined by means of shear waves.

With a combination of both items, the following is possible for instance:

complete MRE examinations of skeletal muscles by recording a plurality of time-resolved wave images within 50 seconds;

recording 16 time-resolved wave images of the human liver with an excellent SNR within 4 breath-holds;

recording shear waves in the human heart, which for the first time allows the use of MRE for measuring myocardial elasticities.

Hence, the method in accordance with the invention (also referred to as fractional MRE) generally opens up the possibility to perform clinically relevant examinations on patients without the considerable time stress linked with conventional MRE, which automatically leads to an acousto-mechanical stress of the persons to be examined.

With the method in accordance with the invention, only part of a motion cycle of the oscillations induced in the tissue is encoded magnetically, whereby a phase difference signal (detected by means of the magnetic resonance for visualizing tissue oscillations) becomes correspondingly smaller. As could be demonstrated, however, this is overcompensated for soft and viscous materials with short transverse relaxation times. In addition, very short imaging times are achievable due to the fractional MRE, as they are required in the presence of a blood stream or with cardiac motions, so that the method of the invention provides for in vivo examinations also of myocardial elasticities.

The detection of tissue oscillations in accordance with the invention primarily refers to the detection of the first harmonic (with the frequency $f_v$) of tissue oscillations, which are generated by a periodic excitation with the frequency $f_v$. It is, however, also possible in principle to detect higher harmonics of the oscillation induced in the tissue.

For a better understanding of the present invention, the relation between decay of the MRT signal and attenuation of shear waves in viscous materials when using a motion encoding gradient will be described below. Since both physical quantities (MRT signal, attenuation of shear waves) are linked with each other in MRE, the derivation of this relation here is referred to as equation of elastography.

As a first step, an analytical solution should be indicated for the encoded phase signal in MRE. This phase signal carries the information of the particle displacement in the tissue. It is measured as a differential signal, i.e. two phase signals with an inverse motion contrast are subtracted from each other, so that motion information exclusively is maintained.

There are assumed spins in a stationary condition of the mechanical oscillations. The spins should oscillate harmonically with a polarization u and a phase $2\pi f_v t+\theta$, wherein $\theta$ is a constant phase offset which depends on the onset of the oscillation excitation and the place of the oscillating particles relative to the oscillation generator.

The phase accumulated during the nth TR, which depends on the harmonic motion, can be calculated as follows:

$$\phi_n = \gamma g \int_{(n-1)TR}^{nTR} G(t)\sin(2\pi f_v t+\theta)dt$$

where $\gamma$ is the gyromagnetic ratio for protons. The gradient G is the sum of the motion encoding gradients $G_{ME}$ and all image-forming gradients which contribute to $\phi_n$.

In the following, a periodic stationary condition of the spin phase $\phi=\phi_n=\phi_{n+N}$ is assumed. In addition, it is assumed that harmonic gradients are used for motion encoding, i.e. $G_{ME}$ has the form $\sin(2\pi f_g t)$. The number of gradient cycles ($n_g$) is equal to the shortest possible $G_{ME}$ with a specified frequency $f_g$. Relaxation has not been taken into account. From the above equation for the phase, the following is obtained for the phase shift $\phi$ maximally achievable by the motion encoding gradient.

$$\varphi = \frac{\gamma G_{ME} u}{\pi f_v} \frac{q}{1-q^2} \sin(\pi q),$$

$$n_s = 1$$

$$q = \frac{f_v}{f_g}$$

$$\theta = \pi(1-q)$$

In an MRE experiment, in which two images are recorded (either with an alternating $G_{ME}$ or with inverse wave amplitudes), the phase difference is twice as large.

The above equation for $\phi$ is indicated for the case that only one single MEG cycle is employed. For the classical case of $f_v=f_g$, $\phi$ converges against the limit value $\gamma Gu/f_v$. For the case of $q\neq 1$, the encoded phase difference is smaller, i.e. the signal in the MRE experiment is weaker than in the classical case, as already mentioned above. However, for a correct estimation of the encoded signal, the effective displacement u inside the organ to be examined must be considered. This can be indicated as follows for a distance X from the oscillation source, when the distance is one wavelength ($X=c/f_v$, with c: velocity of the shear waves in the tissue):

$$u = u_0 \exp\left(-\frac{4\pi^2 \eta n_v}{\sqrt{(\mu TR)^2 + (2\pi \eta n_v)^2} + \mu TR}\right)$$

and $$u \approx u_0 \exp\left(-\frac{2\pi^2 \eta n_v}{\mu TR}\right) \quad \mu TR \gg 2\pi \eta n_v$$

$\mu$ and $\eta$ designate the shear modulus and the shear viscosity, respectively. $u_0$ is the displacement at the point $X=0$.

The above relationship represents a good approximation for the range of viscoelastic parameters examined with MRE, such as liver or skeletal muscles with $\mu=5$ kPa, $\eta=2$ Pas, $f_v=100$ Hz, and $n_v=1$. Typical characteristics for an MEG field include: variable gradient direction in all spatial directions with a (currently) maximum amplitude of 35 mT/m; $f_g$ maximally up to 800 Hz for 35 mT/m; trapezoidal-bipolar form of gradient with $n_g=1$. As base sequence (without motion encoding): balanced SSFP with a TR of about 3-4 ms.

In a further advantageous development of the method of the invention, one period length of the oscillations induced in the tissue corresponds to the repeat time TR of the applied magnetic field or an integer multiple of the repeat time TR.

In addition, it preferably is provided that inducing the mechanical oscillations is effected in synchronism with the magnetic field. Synchronizing TR and $f_v$ is important to ensure that in each imaging step (i.e. in each TR) the signal phase correlates with an identical motion phase. If the above equation is not observed for $f_v$, there will be coherencies between signal phase and motion phase, which disturb the image reconstruction.

To combine short repeat times TR and low oscillation frequencies ($f_v$), the number $n_v$ of oscillation periods during one repetition period TR must become fractional, i.e.:

$$n_v = f_v \cdot TR \leq 1$$

This results in $f_v \leq 1/TR \leq 1/(TR_{min}+1/f_g) < f_g$, wherein $TR_{min}$ is the minimum TR of sequence without motion encoding. A measure for the synchronization between motion encoding and oscillation is provided by the ratio q:

$$q = \frac{f_v}{f_g} = n_v\left(1 - \frac{TR_{min}}{TR}\right)$$

In conventional MRE, q=1, since here $f_v$ is not bound to TR, but to $f_g$. On the other hand, with $n_v \leq 1$ and $TR_{min} > 0$, q always is a fraction of one.

It is particularly advantageous, when for detecting oscillations generated in the tissue
 a first bipolar gradient field is applied to the tissue and a first data record characterizing the phase of the oscillations in the tissue is generated, and subsequently
 a second bipolar gradient field is applied to the tissue and a second data record characterizing the phase of the oscillations in the tissue is generated.

From the respective data records, images can be generated, which represent the phase distribution in the tissue, whereby viscoelastic quantities of the tissue and hence pathological changes of the tissue can be inferred. For this purpose, data of the first and second data records associated to the same portion of the tissue preferably are subtracted from each other, and the result is stored in a further data record (from which e.g. image information can be obtained).

One possibility for generating two images consists in taking two successive images with different gradient fields, with the first gradient field being inverse in time with respect to the second gradient field, so that the first gradient field has a maximum at a specific time measured from the beginning of a period of the gradient field, whereas the second gradient field has a minimum at this time.

Another possibility is provided especially in the method of the invention, when a period of the oscillation induced in the tissue is composed of a plurality of time intervals, which each correspond to the repeat time TR of the magnetic field applied, and during one of the time intervals each a data record (characterizing the phase of the oscillations in the tissue) associated to the respective time interval is generated by detecting the magnetic field emerging from the tissue.

For instance, a period of the oscillation induced in the tissue can be composed of first and second time intervals each with a length TR, wherein
a) a first data record associated to the first time interval is generated;
b) a second data record associated to the second time interval is generated, wherein the data of the first and second data records each are associated to specific portions of the tissue; and
c) data of the first and second data records each associated to the same portion of the tissue are subtracted from each other.

This method is particularly advantageous, since the polarity of the gradient field does not have to be changed for taking several images, but the same gradient field is used for each image.

In a particularly advantageous development, inducing mechanical oscillations in the tissue is effected by means of the above-described device in accordance with the invention. Accordingly, an MRE method is available, which can be performed quickly and easily. It should be noted, however, that the use of such excitation device is advantageous, but the same is not absolutely necessary for performing the method in accordance with the invention.

Generating the tissue oscillations can be effected by loudspeakers beside all other apparatuses which directly or indirectly generate a periodic motion. In a second aspect, this invention comprises a device for generating mechanical oscillations in an examination object using magnetic resonance elastography (MRE), comprising
 a step motor for generating a periodic motion, and
 a transmission element for transmitting the periodic motion of the step motor to the examination object, in order to generate mechanical oscillations in the same.

By means of a step motor, the high accuracy and stability of the oscillating motion necessary for synchronization with the motion encoding gradient can be ensured. In the case of rigid materials (tubes, rods, bars), coupling to a transmission element can for instance be effected by means of eccentric disks. In addition, a hydraulic system can be provided for generating oscillations, wherein e.g. for coupling to a transmission element an eccentric can be attached to a hydraulic piston or to some other component of the hydraulic system.

FIG. 1A shows a patient 1 as examination object of an MRE examination in a clinical tomograph 2. The tomograph 2 includes a magnet 21 for generating static and periodic magnetic fields in a tissue of the patient 1 to be examined. The magnet 21 includes a receiving aperture 211 for receiving the patient 1.

In the magnet 21, all systems are accommodated which are necessary for generating the static magnetic field and the periodic magnetic field (for resolution and for energetic excitation of the hydrogen nuclei). These systems include a closed superconducting coil 212, coils 213 for magnetic field gradients briefly switchable in 3 orthogonal spatial directions for resolution (also for generating a motion encoding gradient), and a main excitation coil 214 for polarizing the hydrogen nuclei.

The homogeneity of all magnetic fields generated with the different coils 212-214 is decisive for the image quality. Therefore, disturbances of these magnetic fields for instance by metallic objects must carefully be excluded.

The excitation of mechanical oscillations in the tissue to be examined, which is necessary for an MRE examination, is generated by a motion source 3, which is arranged at a distance from the tomograph 2. The motion source 3 comprises a loudspeaker membrane 312 which can be set in periodic oscillations.

The motion of the loudspeaker membrane 312 is transmitted to the patient 1 via a transmission element in the form of a tube 4 with an optimized ratio of flexural rigidity and weight, which is connected with a joint 311. Via the joint 311, one end 41 of the tube 4 is directly coupled with a surface of the loudspeaker membrane 312, so that the oscillations are directly transmitted to the tube via the joint 311, without an interposed gaseous medium being involved.

By means of the joint 311 and the possible angled position of the tube 4 (and hence of the power transmission) with respect to the primary displacement direction of the loudspeaker membrane 312, the tube 4 can flexibly be positioned at the patient in the vicinity of the tissue to be examined. This flexibility necessary for an optimal coupling of mechanical oscillations into the tissue to be examined is promoted in addition by the movable supporting rack 32.

The motion source 3 has a modular construction. The loudspeaker membrane 312, for instance, is part of a loudspeaker 31 which is mounted in a hermetically sealed housing 33. The housing 33 has standardized dimensions and together with the loudspeaker 31 forms a loudspeaker module 35, which is replaceably mounted on a non-magnetic supporting rack 32. Due to this construction of the motion source 3, it is possible to quickly and easily replace one loudspeaker module by another, so that depending on the kind of tissue to be examined, different loudspeakers (depending on the required excitation frequency) can be used.

The supporting rack 32 is stabilized by sand weights, but is easily movable via rollers 34 mounted on its bottom surface. Due to the fact that the motion source 3 is erected at a distance from the tomograph 3, mutual interactions and disturbances between the loudspeaker magnet and all magnetic fields necessary for the MRT examination are excluded.

For activating the loudspeaker membrane 31, a function generator 5 is used, which is electrically connected with the loudspeaker membrane 31 via an amplifier 6. The function generator 5 is controlled via a control computer 7, which in turn forms part of a control of the tomograph 2.

A few characteristics of a device in accordance with the embodiment described above are listed below:
Impedance of the loudspeaker: 2-16 Ohm
Max. stroke of the loudspeaker membrane: 1-60 mm (without load, depending on the loudspeaker used).
Power: 100 W-2 kW permanent load (depending on the loudspeaker used).
Materials: except for the loudspeaker magnets used in both modules, all parts are made of non-magnetic materials.
Supporting rack: wood, non-ferrous metals, PVC, sand
Modules for generating motion: wood, magnesium, PVC, stainless steel, epoxy resin
Joint: plastics, rubber
Transmission tube: carbon fiber
Transmission heads: wood, PVC, nylon, carbon fibers It should be appreciated that the values only are exemplary and can easily be changed, if this is required by a particular application of the device.

FIG. 1B shows a similar MRE tomograph as FIG. 1A. In a tomograph 2, a patient 1 is located. A motion source 3 for generating mechanical oscillations in a tissue of the patient 1 is installed at a distance d from the tomograph 2. In this embodiment, the distance is more than 2.5 m, in order to safely exclude a disturbing interaction of the loudspeaker magnet with the magnetic fields of the tomograph. It should be appreciated that this distance can vary depending on the configuration of the motion source and the tomograph, i.e. can also be less than said 2.5 m.

FIG. 2A shows a detailed view of a loudspeaker module 35 for use in a motion source as described in FIG. 1A, 1B. The loudspeaker module 35 includes a doubly supported loudspeaker 31, which is arranged in a closed housing 33. The loudspeaker 31 has a loudspeaker membrane 312 and for generating a periodic membrane motion a drive comprising a magnet 313 and an induction coil 314, which is unchanged as compared to an ordinary loudspeaker. For activating the loudspeaker 31, electrical connections 315 also are provided, via which the loudspeaker can be connected with a control unit (not shown).

The loudspeaker 31 is modified, however, with respect to the features required for a direct transmission of oscillating motions. For power transmission over a rather large area, which is advantageous for a high stability and ruggedness with respect to the occurring forces, an additional stabilizing sleeve 316 is integrated. A transmission element constituting a rod 400 is connected with the loudspeaker membrane 312 via mounting means in the form of an adhesive 320, a plastic supporting plate 321 and a threaded pin 322.

The loudspeaker membrane 312 together with the plastic supporting plate 321 is glued into the loudspeaker 31 by using the adhesive 320 so as to cover a large area and fill the gaps. The joint 311 is anchored in the supporting plate 321 and in the adhesive 320 via the threaded pin 322 by using the plastic supporting plate 321.

The connection via the above-described mounting means is configured such that oscillations of the membrane are directly passed on into the transmission rod via the mounting means (adhesive, supporting plate, joint), without the oscillations first being transmitted via a gaseous medium such as air.

At a joint head 3111, one end 41 of the rod 400 is fixed for transmitting oscillations. At its end 403 opposite the joint 311, the rod 400 has a variable, easily replaceable end piece 44, with which the oscillating motions are transmitted into the examination object by direct contact. The end piece 44 is fixed at the rod 400 by means of screw connections and easily replaceable. The shape of the end pieces thereby can variably be optimized for the respective examination object. Designs vary from a simple ball head over bite blocks to the drive of direction reversal systems or the force reversal to special downstream transmission mechanisms (see FIG. 4, 5).

Figure 2B:
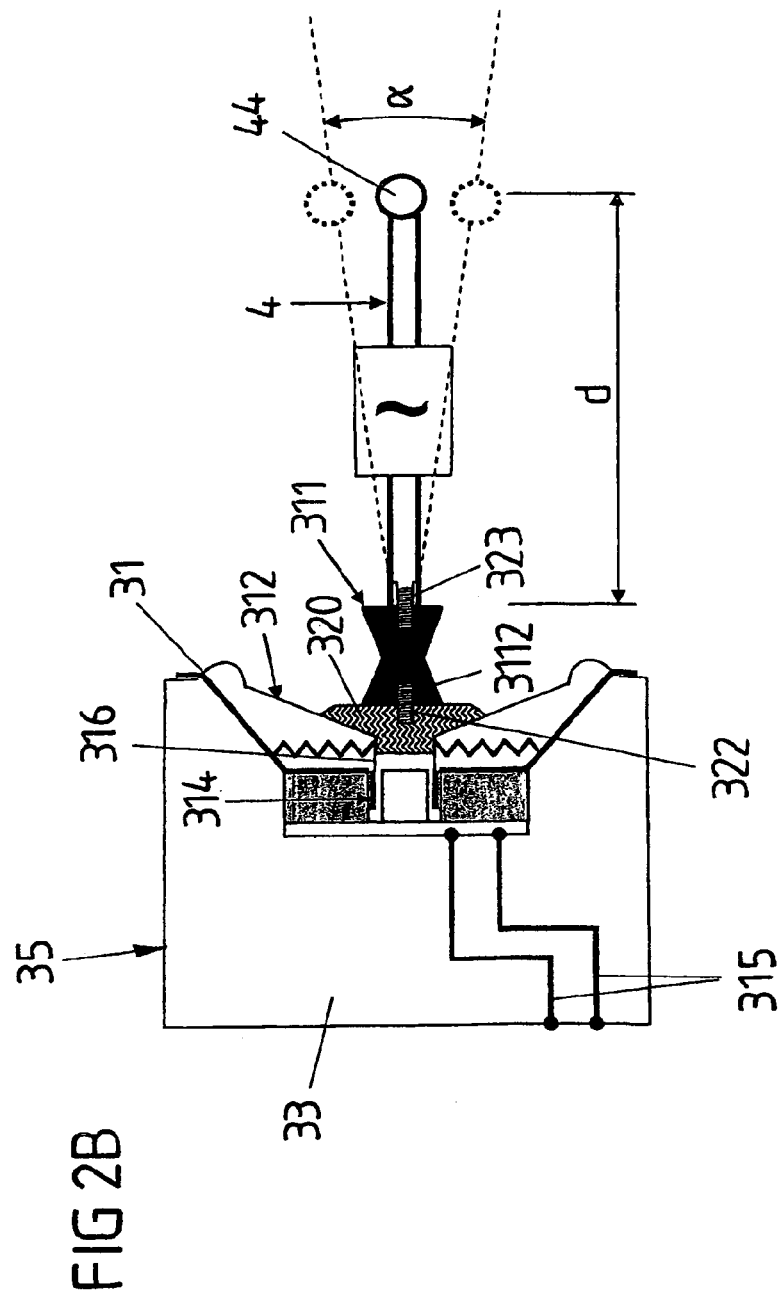
FIG. 2B shows a second variant of the oscillation generating device.

FIG. 2B shows a further embodiment of the device in accordance with the invention. As in FIG. 2A, a loudspeaker module 35 includes a loudspeaker 31 arranged in a housing 33. A portion 3112 of a joint 311 is connected with a membrane 312 of the loudspeaker 31 by means of an adhesive 320. The connection is made via a first threaded pin 322, one end of which protrudes into the adhesive 320. On its side facing away from the loudspeaker membrane 312, the joint 311 is connected with a tube 4 as transmission element. In contrast to the loudspeaker module of FIG. 4, the connection of the joint 311 with the tube 4 is effected via a second threaded pin 323.

By means of the joint 311 it is possible to swivel the tube 4 at an angle α in the range between +10° and −10°. This provides for a more flexible positioning of the loudspeaker module 35 with respect to a tomograph (not shown in FIG. 2B; cf. FIG. 1B). The distance d of the loudspeaker module 35 to the tomograph can be 2-4 m.

In FIG. 3, a further embodiment of the device is shown in detail, namely a loudspeaker module 35 which is formed for an indirect generation of a periodic motion of a loudspeaker membrane. The loudspeaker module 35 consists of a closed housing 33 with electrical connections 315 and a doubly supported first loudspeaker 31 with a loudspeaker membrane 312, which is coupled to a transmission element in the form of a tube 4.

In this loudspeaker module, however, the loudspeaker membrane 312 is a passive membrane, since the loudspeaker 31 does not have its own drive. The (passive) loudspeaker membrane 312 is driven by a second loudspeaker 30 with an (active) loudspeaker membrane, which in the generally closed system (housing 33) generates periodic pressure fluctuations, which are followed by the airtight passive membrane 312.

The power transmission from the passive membrane 312 via the tube 4 and a transmission head 44 to a patient (not shown) is effected in the manner described already. Like the membranes of FIG. 2A, 2B, the passive membrane 312 includes an additionally integrated stabilizing sleeve 316, a plastic supporting plate 321 fixed with adhesive 320, and a joint 311 screwed into the same. The tube 4 and the transmission head 44 are universally applicable for all modules.

FIG. 4 shows an end piece 45 for transmitting mechanical oscillations into a brain parenchyma. In this component, particular importance was attached to a simple application for examinations on patients and short preparation times. Individual adaptations, as they are necessary for instance with bite blocks, thereby can be omitted.

By means of a positive fit 441 and a screw connection 442, the mechanical oscillations are transmitted by a transmission tube 4 via a joint head 453 into the end piece 45. The central part of the end piece 45 is a stable plastic tube 454, in which rests the head 11 of a person to be examined. On the plastic tube 454 provided with windows 455 a roller 456 is mounted beside the joint head 453, with which the horizontal primary motion of the transmission tube 4 is converted into an up-and-down motion of the head 11. The roller 456 is movably mounted, in order to shift the end piece 45 with respect to a contact point 357 of the head 11. This is necessary to ensure a maximum possible excitation of the tissue to be examined. The transmission of motion into the head becomes minimal, when the pivot point of the roller and the contact point 357 of the head 11 are on top of each other.

FIGS. 5A, 5B show different views of an end piece 46 for the variable transmission of mechanical oscillations into a multitude of tissues. By means of a positive fit 441 and a screw connection 442, the linear motion of a transmission tube 4 is transmitted via a ball head 461 to an excitation rod 462 of the end piece 46. The excitation rod 462 ends in a transmission head 465, which likewise is variable in shape and size and for generating oscillations is in direct contact with the body surface of a patient (not shown).

The excitation rod 462 is mounted in a plastic ball joint 463 by means of a bearing unit 467, wherein the bearing unit 467 is connected with a horizontal attachment 468 of a positioning rack 464. The horizontal attachment 468 is connected with a base plate 470 via a vertical spacer rod 469.

To ensure a variability as high as possible, the following possibilities exist for changing the position of the transmission head:

Vertical fine adjustment of the excitation rod 462 by means of a clamping screw 466 at the ball joint 463.

Horizontal fine adjustment of the excitation rod 462 due to the movability of the bearing unit 467 relative to the horizontal attachment 468.

Vertical coarse adjustment of the bearing unit 467 by means of spacer rods 469 of different lengths.

Horizontal coarse adjustment due to the movability of the spacer rods 469 on the base plate 470.

Figure 6:
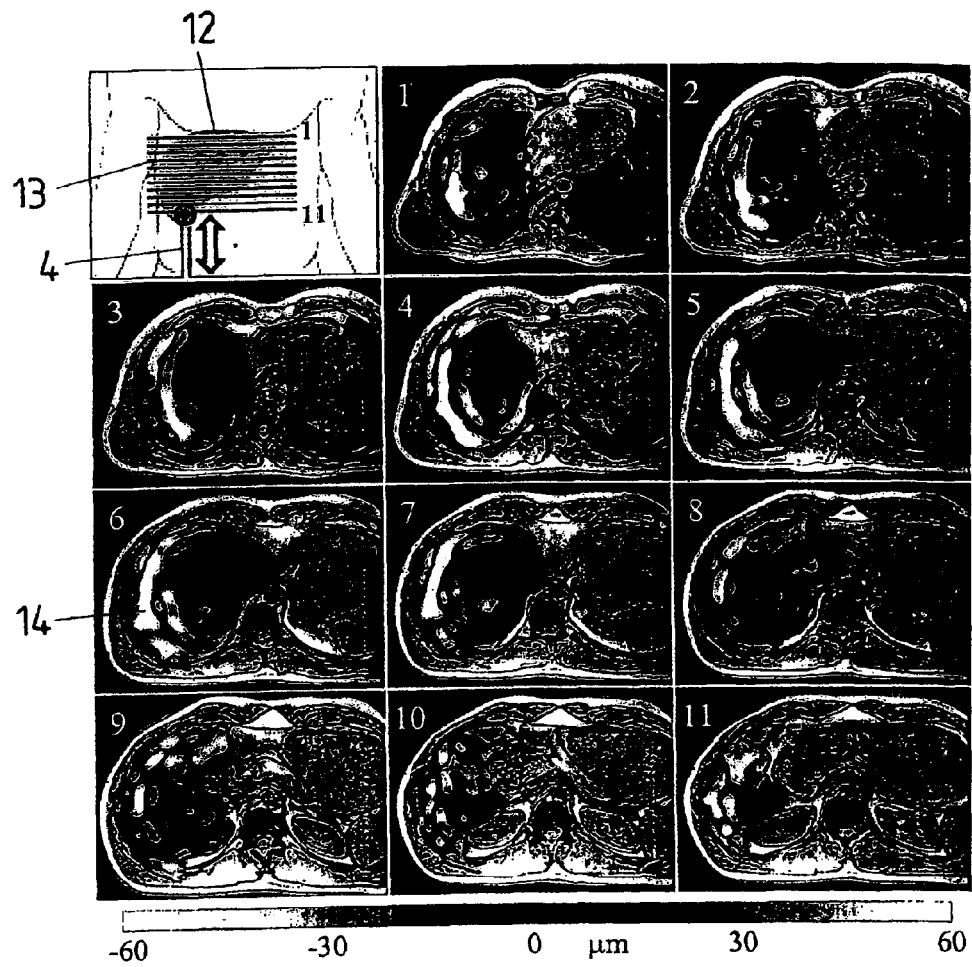
FIG. 6 shows a representation of shear waves generated by means of MRE in a liver.

FIG. 6 shows a series of images of a tissue (liver), which were generated by means of an MRE examination by using the device in accordance with the invention for generating oscillations. The partial image a) shows that oscillations were coupled into the liver 12 of a patient 1 via a transmission rod 4. By means of magnetic resonance, the oscillations were detected and a gray-scale image was generated, wherein the gray values correspond to different phase conditions of the mechanical oscillations induced in the liver (in the form of shear waves). Such images were generated for various sections 13 (numbered from #1-11) through the liver 12 of the subject (the partial images of FIG. 6 each show an MRE image associated to one of these sections).

Figure 7:
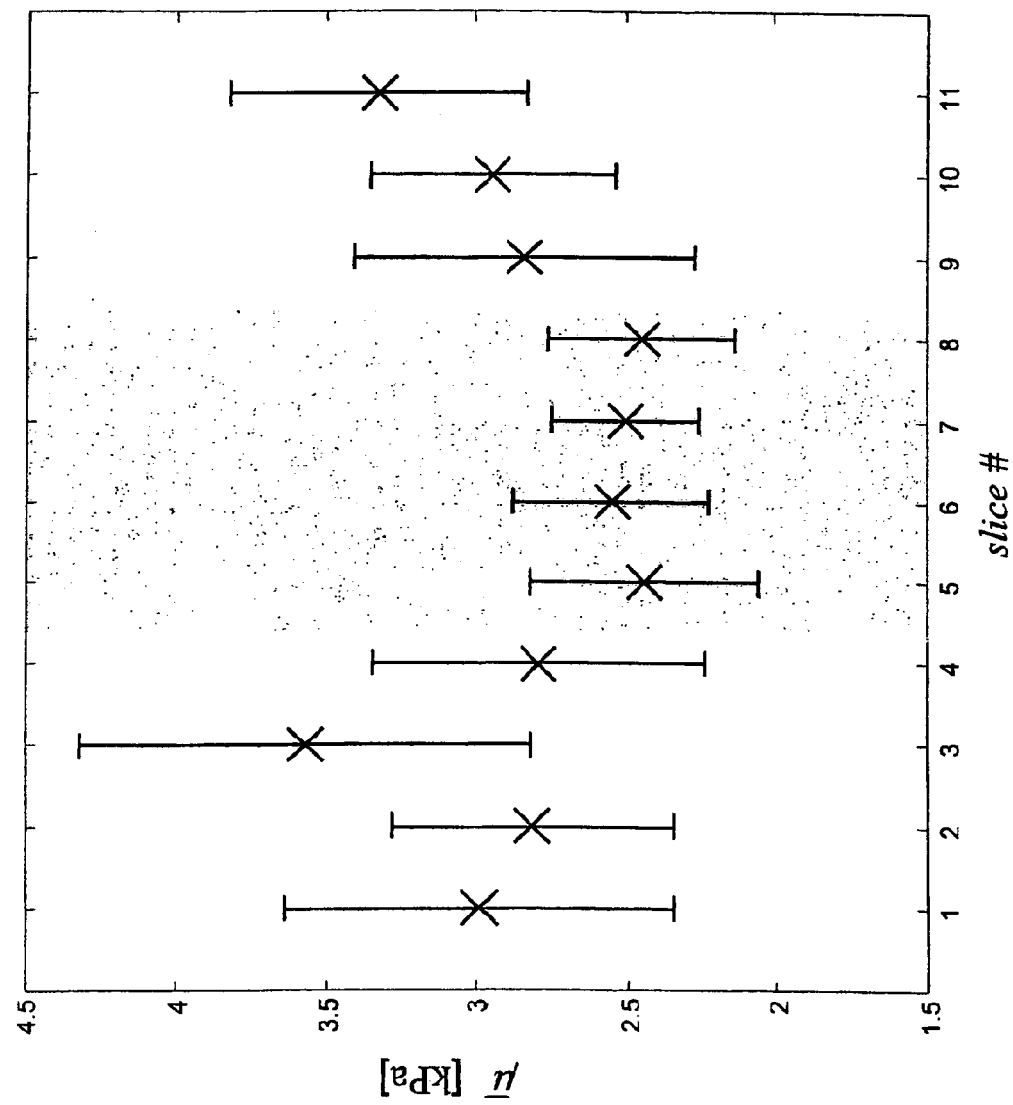
FIG. 7 shows an evaluation of the MRE examination represented in FIG. 6.

The bright regions 14 of one gray-scale image each represent minima of the shear waves. From the gray-scale images, the wavelength of the shear waves generated in the tissue thus can be determined for instance by determining the distance of two adjacent bright spots 14. From the wavelength, viscoelastic characteristics of the tissue can in turn be determined. This is shown in FIG. 7 for the respective sections (X-axis, #1-11) of FIG. 6. The shear modulus is plotted on the Y-axis, so that a shear modulus is associated to each section #1-11 through the liver. If a value falls out of the normal range (as in the case of sections #5-8), this is a sign for a pathological change of the respective tissue portion.

FIG. 8A shows the principle of a classical MRE experiment, according to which mechanical oscillations with a frequency $f_v$ are induced in a tissue. Motion sensibilization (motion encoding) is effected via bipolar motion gradients $G_{ME}$ (with the frequency $f_g$), which are part of a magnetic field sequence for detection of the tissue oscillations. The MRT sequence has a repeat time TR. In the conventional MRE method shown in FIG. 8A, the frequency $f_g$ of the motion gradient $G_{ME}$ corresponds to the frequency $f_v$ of the mechanical oscillations, so that $$f_v > \frac{1}{TR}.$$

In two successive experiments A, B, the polarity of the motion gradient $G_{ME}$ is reversed, in order to obtain a phase contrast $\Delta\phi$, which only depends on the encoded motion (of the generated mechanical oscillation). For this purpose, the data (characterizing the phase of the oscillations) which were generated in the respective experiments A, B are processed with each other, e.g. subtracted from each other.

FIG. 8B shows the principle of the method in accordance with the invention, in which $$f_v \leq \frac{1}{TR},$$

in contrast to the classical method of FIG. 8A. FIG. 8B shows three different oscillation modes for the polarization vector u (of the mechanical oscillation). The oscillation modes are characterized in that the number $n_v$ during a repetition period TR represents different fractions of the value one: $n_v=1(f_v=1/Tr)$, $n_v=\frac{1}{2}(f_v=1/(2TR))$ and $n_v=\frac{1}{4}(f_v=1/(4TR))$. The asterisk designates a trigger for the wave generator (in order to synchronize the mechanical oscillations with the MRT sequence). For $n_v=1$, two separate experiments with opposite $G_{ME}$ polarities must be made, in order to calculate $\Delta\phi$ (see FIG. 8A). For nv=½ and nv=¼, the phase images for the subtraction are recorded by interleaving ($\Delta\phi$=A−B or $2\Delta\phi$=A−C+i(B−D)).

Figure 9A:
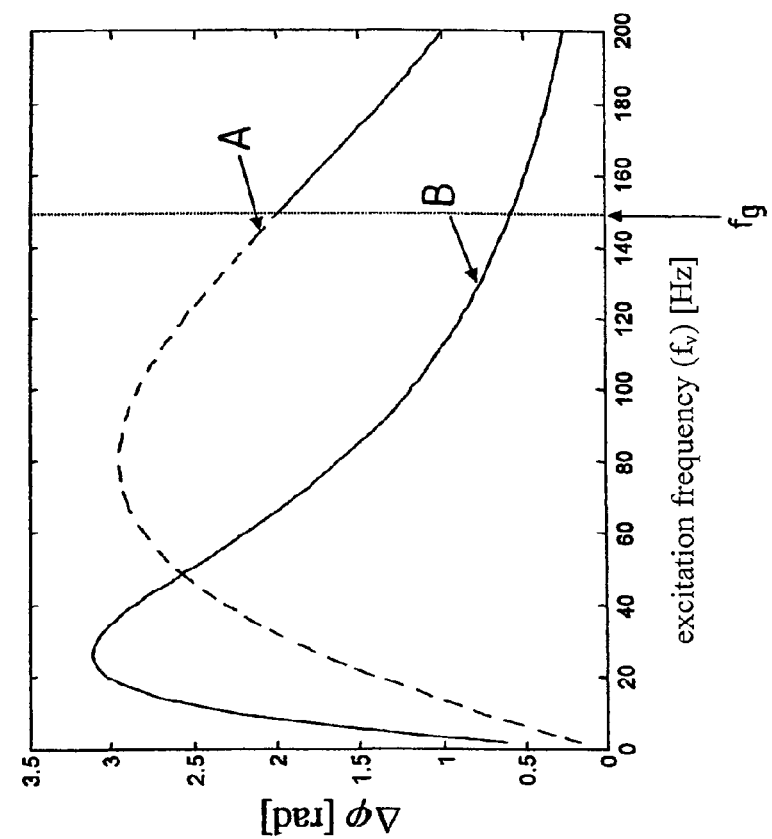
FIG. 9A, 9B show a determination of a phase difference signal for various excitation frequencies.

FIG. 9A shows a phase difference signal $\Delta\phi$ in MRE for various tissues (muscle and liver tissue A, B). The motion encoding gradient MEG has a frequency $f_g$=150 Hz. It can clearly be seen that the maxima of the two curves are reached far below the MEG frequency $f_g$. This means that the use of smaller excitation frequencies for generating tissue oscillations ($f_v < f_g$) is advantageous. In particular, a loss in the phase signal is at least compensated by encoding only a fraction of the oscillation period (as in the method of the invention).

Figure 9B:
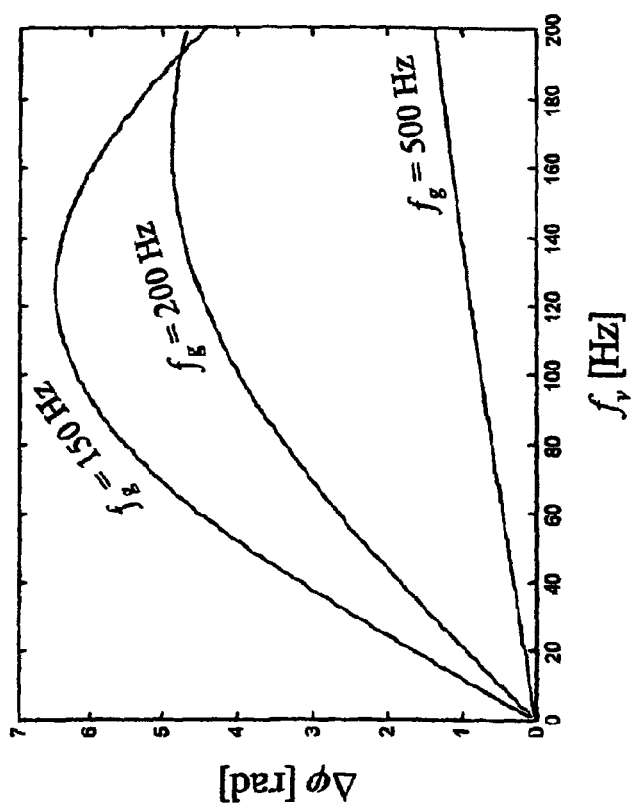

FIG. 9B likewise shows the dependence of the phase difference signal $\Delta\phi$ in dependence on the excitation frequency $f_v$ for various encoding frequencies $f_g$. Again, it can be seen that with excitation frequencies $f_v$ the maximally achievable phase difference each lies below $f_g$.

Figure 10A:
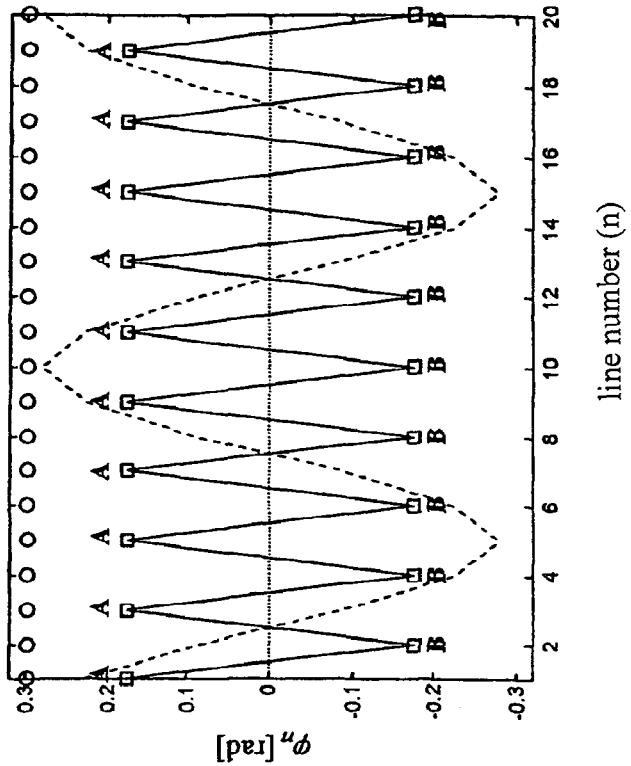
FIG. 10A, 10B show the course of the spin phase for various magnetic field gradients.
Figure 10B:
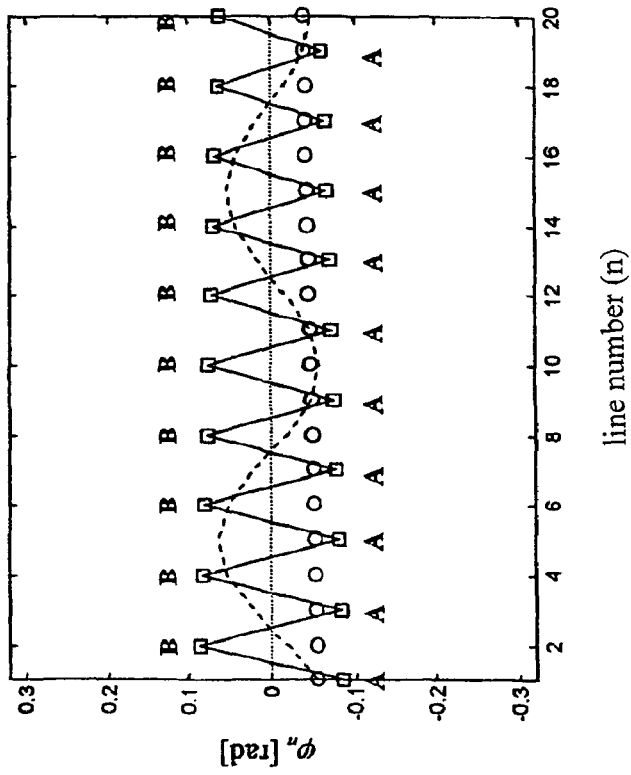

FIGS. 10A, 10B illustrate the principle of the detection of tissue oscillations by means of magnetic resonance. FIG. 10A shows a portion of the spin phase $\phi_n$ which originates from a phase encoding gradient, and FIG. 10B shows a portion of the spin phase $\phi_n$ which originates from a (bipolar) motion encoding gradient. The phase encoding gradient is decreasing linearly with the line number n, whereas the bipolar motion encoding gradient has a constant amplitude. Three different oscillation modes are observed: With $n_v=1$ (circular symbols) a phase shift occurs, which is proportional to the strength of the phase encoding gradient. With $n_v=\frac{1}{2}$ (square symbols), a periodically changing phase shift is obtained, which is utilized for allocating even or odd line numbers to different images A, B.

The dashed curve corresponds to $n_v=0.9$, i.e. a frequency mismatch between 1/TR and $f_v$. This leads to a "beat" (or interference) of $\phi_n$ with a period TR/0.1. The dotted line represents the spin phase of static particles.

Figure 11A:
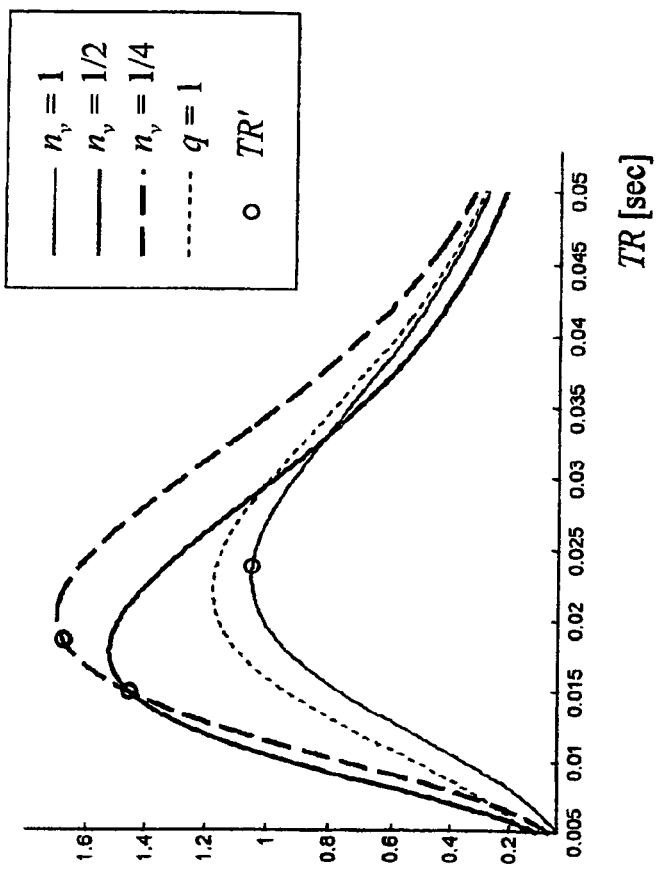
FIG. 11A, 11B show a representation of a calculated phase-to-noise ratio PNR for various repeat times.
Figure 11B:
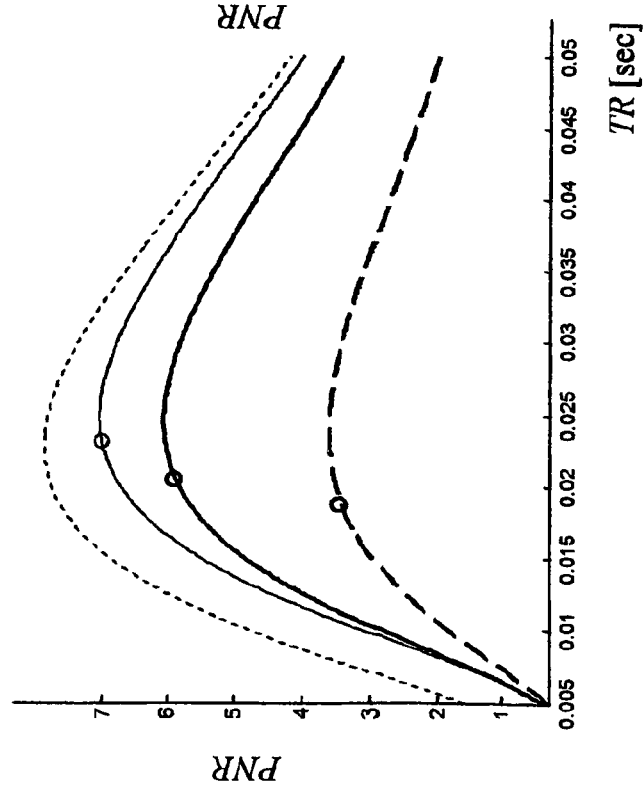

FIGS. 11A, 11B show a calculated phase-to-noise ratio (PNR) for two viscoelastic materials with different $T_2^*$ relaxation times, in order to model muscle tissue (FIG. 11A with $\mu$=5000 kPa, $\eta$=2 Pas, $T_2^*$=17 ms) and liver tissue (FIG. 11B with $\mu$=2000 kPa, $\eta$=4 Pas, $T_2^*$=9 ms), respectively. For comparison, a dashed curve represents a classical MRE experiment, according to which the oscillation frequency $f_v$ and the encoding frequency $f_g$ coincide, i.e. $f_v=f_g=1/TR$ ($TR_{min}=0$). The open circles each designate an optimum repeat time TR', which is obtained from the PNR:

$$TR' = \frac{1}{2}T_2^* + \frac{1}{2}\sqrt{T_2^{*2} + 8\pi^2 T_2^* n_v \frac{\eta}{\mu}}$$

Further simulation parameters include: $|u_0|$=100 μm; $|G_{ME}|$=20 mT/m (muscle tissue), 35 mT/m (liver); $SNR_0$=11; $TR_{min}$=3.4 ms (muscle), 3.2 ms (liver.

Figure 12:
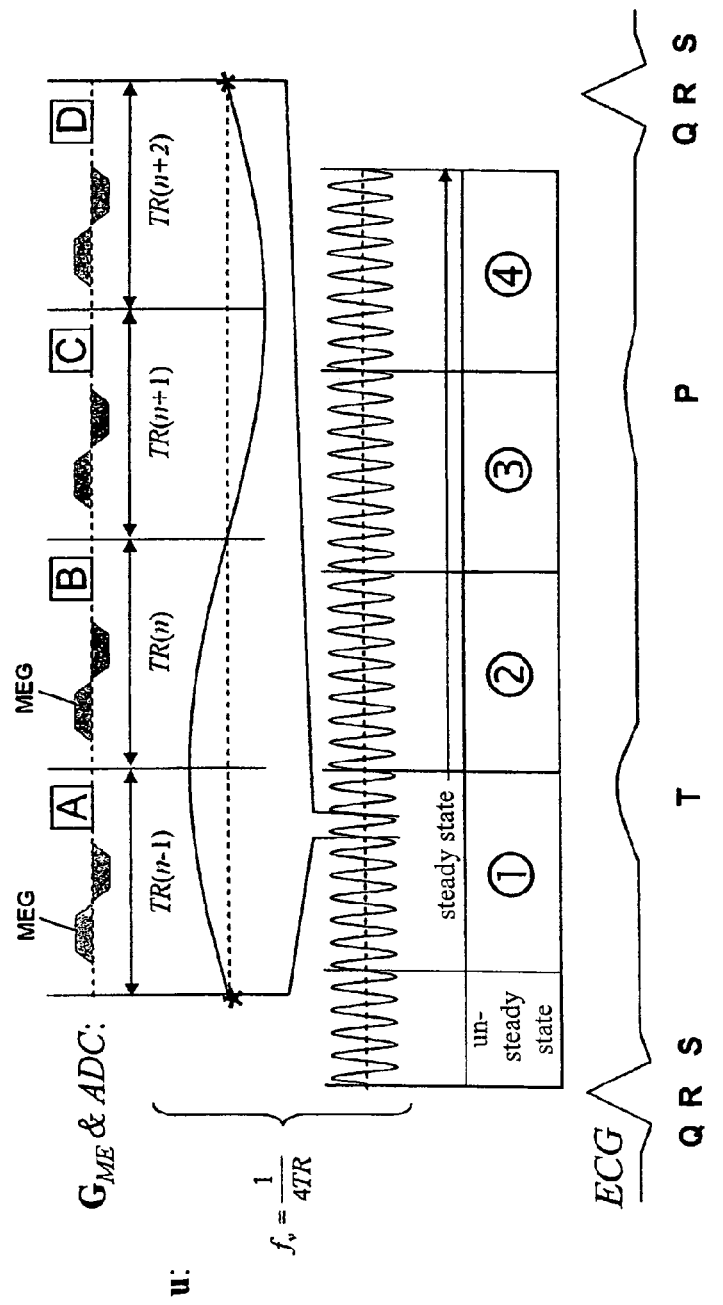
FIG. 12 shows a time protocol of an in-vivo myocardial MRE.

FIG. 12 shows a time protocol of an in-vivo myocardial MR elastography. Due to the high amount of internal motions, it is necessary here to choose a low amount of encoding ($q \approx 0.1$, $n_v=\frac{1}{4}$). In addition, the phase encoding of the k-space is divided into 8 segments with 9 lines, which are recorded within 8 heart cycles. As a result, 4×4 interleaved phase images are obtained, which are composed to obtain 4 complex phase difference images, which are each associated to the cardiac phases ①  to ④ in FIG. 12.

Figure 13A:
FIG. 13A, 13B show a result of a bSSFP MRE measurement on a human biceps.
Figure 13B:
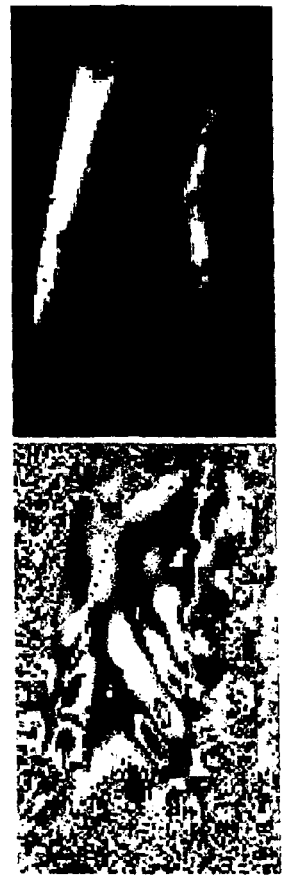

FIGS. 13A, 13B show a result of a bSSFP MRE measurement on a human biceps by using excitation frequencies for shear waves of 120 Hz (FIG. 13A) and 75 Hz (FIG. 13B) and $n_v=1$. The upper images each show the amplitude of the shear waves (translated into gray values), and the respectively lower images show the phase difference. Due to the smaller amplitude of the motion encoding and the shorter repeat time ($u_3$=50 μm; q=0.6), no banding artifacts are observed in FIG. 13A in contrast to FIG. 13B. In FIG. 13B, voids and phase wrapping artifacts can be seen (excitation amplitude $u_3$=150 μm; q=0.75). The PNR of the measurement of FIG. 13B is about 2.3 times as high as the PNR of the measurement of FIG. 13A, which is due to the extension of the motion encoding gradient from 5 to 10 ms and the greater excitation amplitude.

The measurement (as also the measurements described below) was performed with a 1.5 T scanner. The bSSFP sequence is a conventional sequence, to which the described motion encoding gradient is added (trapezoidal, bipolar with variable direction, with frequency and amplitude between the phase encoding and read-out gradients). The oscillation phase was coupled with the MR image by triggering the wave generator at the beginning of every Nth TR cycle (N=number of interleaved images); cf. FIG. 8A, 8B.

20 wave images with alternating amplitude of the motion encoding gradient were recorded, in order to obtain 10 Δϕ images by complex image subtraction, cf. "Bernstein M A, King K F, Zhou X J. Handbook of MRI pulse sequences. Burlington: Elsevier Academic Press; 2004". The wave trigger was shifted 10 times, in order to run through the phase offset θ from π/5 to 2π. The data recording was repeated after 2.5 s each, which results in a measurement time of 50 s. Further sequence parameters include: $|G_{ME}|$=20 mT/m along the cutting direction; FoV=250 mm; 128×128 matrix; section thickness: 5 mm; α=±50°; coronal image plane through a longitudinal axis of the muscle.

The data evaluation for deriving elastic parameters was effected by applying a group-velocity inversion method as described in Papazoglou S, Rump J, Klatt D, Hamhaber U, Braun J, Sack I. Group-velocity inversion in MR elastography on skeletal muscles. In: Proceeding of the 14$^{th}$ Annual Meeting of ISMRM. Seattle. 2006.

Figure 14:
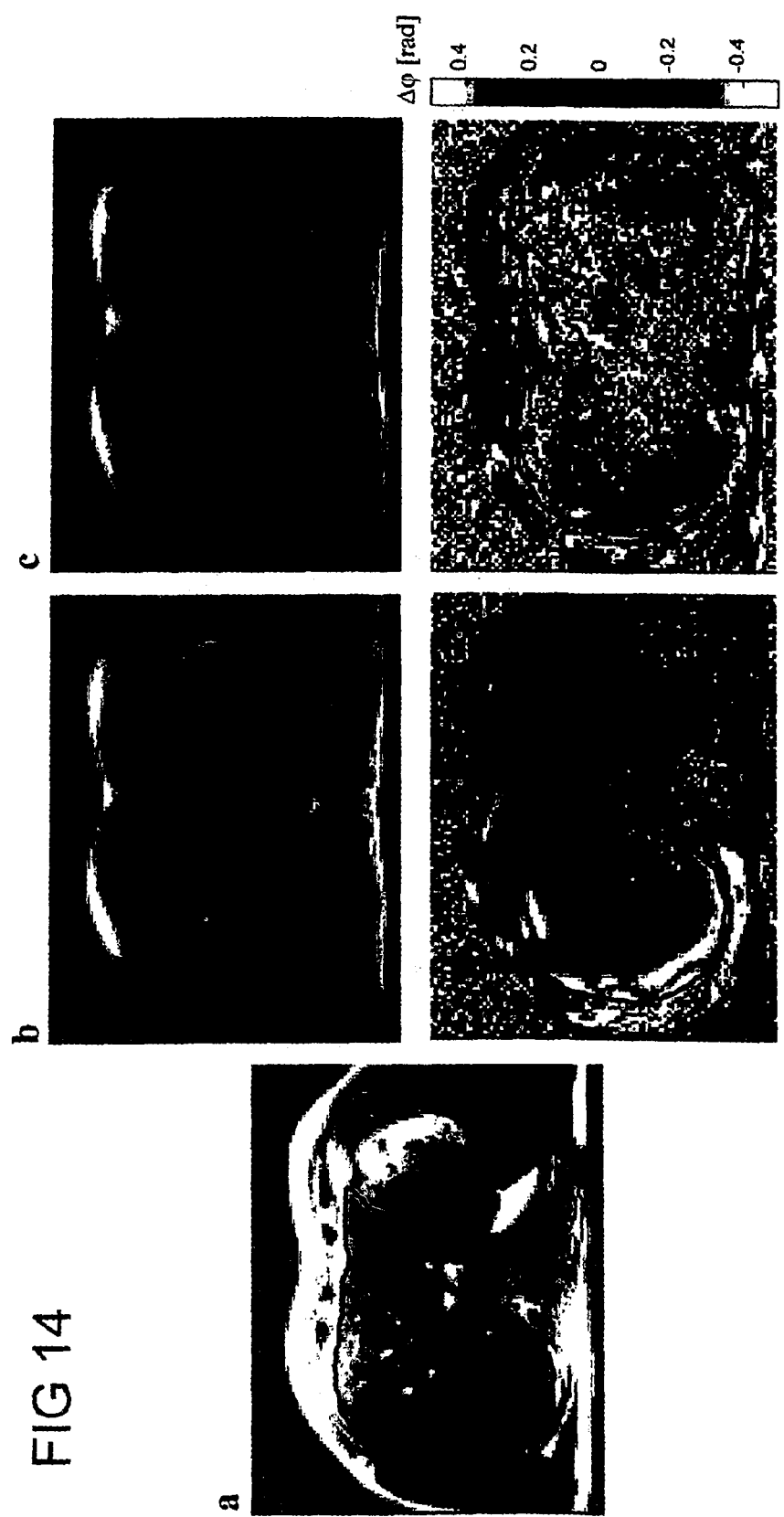
FIG. 14 shows a result of an in-vivo bSSFP MRE experiment with a human liver.

FIG. 14 shows the result of an in-vivo bSSFP MRE experiment on a human liver. The image designated with a) was recorded in one plane (with respect to the human body), without applying a motion encoding gradient, i.e. $TR=TR_{min}$=3.2 ms. The images designated with b), c) of FIG. 14 are bSSFP MRE images of the same section as image a), but a motion encoding gradient was applied to the liver with $f_v$=51 Hz and $n_v=\frac{1}{2}$, TR=9.85 ms (partial image b)) and $f_v$=76 Hz and $n_v=1$, TR=13.2 ms (partial image c)).

The upper images each represent the MRE amplitude. There can be seen a strong decrease in signal intensity, which is due to $T_2^*$ dephasing with long echo times. Although the SNR (signal-to-noise ratio) is particularly low in the images c), the PNR inside the liver still is high enough to reconstruct elastic parameters by inversion of the wave equation. The PNR in the images b) is greater than in the images c), although the frequency mismatch of motion encoding and (mechanical) oscillations is greater (q=0.34 in b) as compared to q=0.76 in c)).

The data obtained were processed by extracting the first harmonic oscillation from the Fourier space at $f_v$ (see Sinkus R, Lorenzen J, Schrader D, Lorenzen M, Dargatz M, Holz D. High-resolution tensor MR elastography for breast tumour detection. Phys. Med. Biol. 2000; 45(6):1649-1664). The complex data were entered in a program for linear inversion, which is based on an algebraic inversion of the wave equation with viscosity (see Catheline S, Gennisson J L, Delon G, Fink M, Sinkus R, Abouelkaram S, Culioli J. Measuring of viscoelastic properties of homogeneous soft solid using transient elastography: an inverse problem approach. J Acoust Soc Am 2004; 116(6):3734-3741).

The viscosity of the liver was estimated by means of the dispersion function of the wave velocity at an estimated $f_v$=51 and 76 Hz by using Voigt's viscoelastic model; cf. Lai W M, Rubin D, Kreml E. Introduction to Continuum Mechanics: Butterworth Heinemann Ltd; 1994. 570 p.

Figure 15:
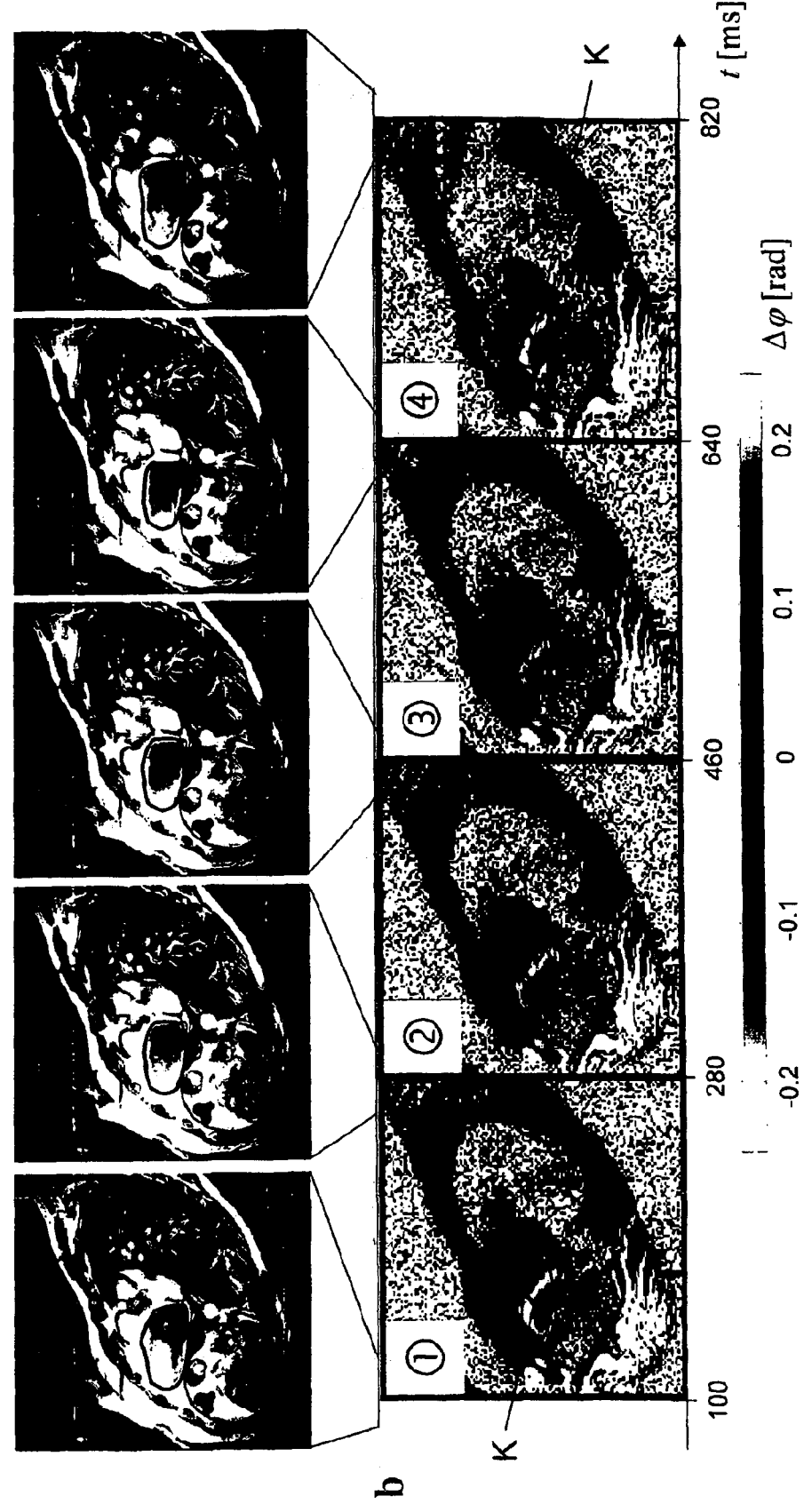
FIG. 15 shows transmural waves recorded by means of MRE in an intraventricular septum.

The images of FIG. 15 show transmural waves in the intraventricular septum (IVS) of a subject, which were excited externally by 50 Hz oscillations of the chest. The images designated with a) are Cine-bSSFP MRI images for anatomic comparison. The location of the IVS is indicated by the continuous line. In this region, the myocardium extends inside an image plane with a thickness of 5 mm. The time resolution of the images in a) is approximately 40 ms.

The phase difference images of the images b) with a time resolution of approximately 180 ms show the externally induced oscillations in the IVS. The oscillations were encoded with bipolar motion encoding gradients with 500 Hz along the section plane. Loudspeaker motions were transmitted to the chest via a transmission rod. The oscillation strength was adjusted corresponding to the subjective feeling of the subject.

The maximum oscillation amplitude was estimated to be 40 μm, since due to the contribution of the image gradients to Δφ an exact calculation would require the complete knowledge of all components of the displacement polarization u. The arrows K indicate the direction of propagation of the shear waves.

Figure 16:
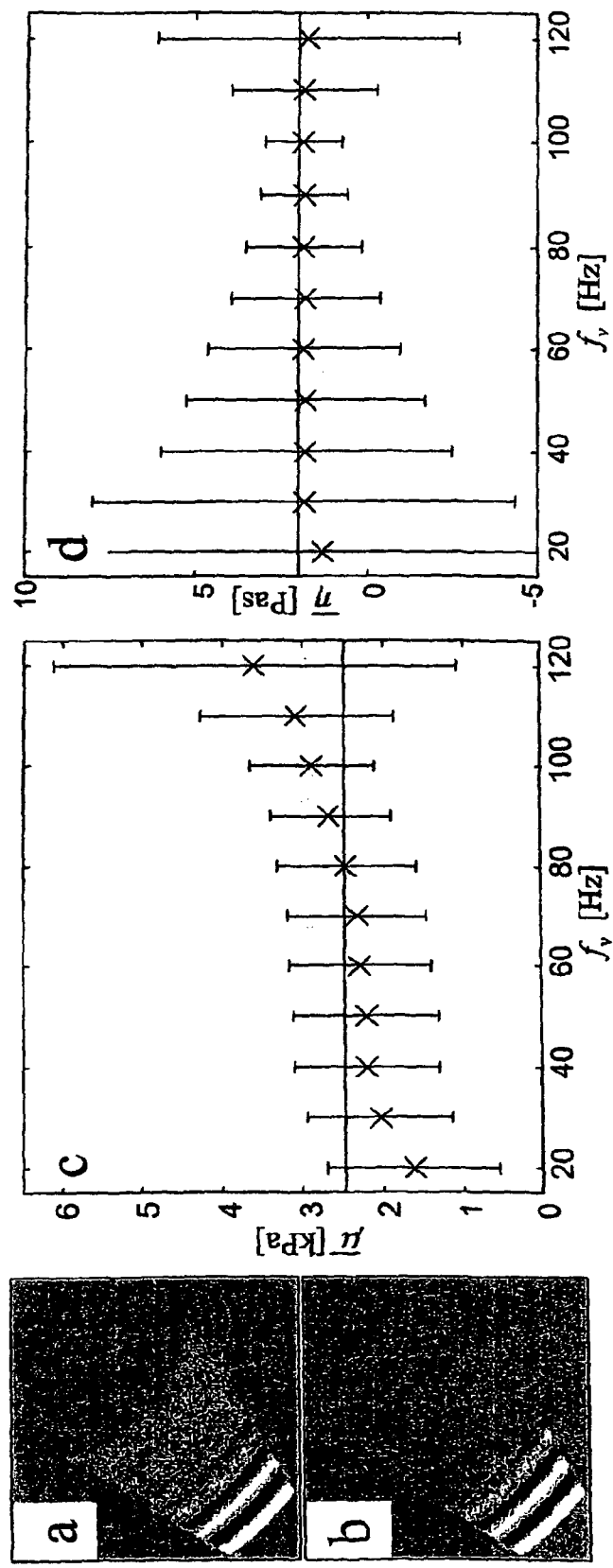
FIG. 16 shows an exemplary representation of tissue shear waves in MRE.

FIGS. 16a-6 show the principle of the MRE evaluation. Shear waves are coupled into a tissue and detected by means of magnetic resonance (FIG. 16a, b). The bright regions in FIG. 16a, b represent regions of maximum amplitude of the shear waves. A computer-implemented evaluation algorithm can be used to filter the MRE data prior to the pictorial representation. For instance, a threshold value for the oscillation amplitudes (i.e. the amplitude of the shear waves) to be represented can be set, in order to filter out amplitudes which lie below the threshold value. The amplitude threshold value in FIG. 16b is greater than in FIG. 16a, which is why the illustrated shear wave "stops" after a shorter distance as compared to FIG. 16b.

FIGS. 16c, d show values for the shear modulus μ and the viscosity η obtained from MRE measurements at various excitation frequencies $f_v$. The determination of these quantities is effected by evaluation of the representation of the shear waves in the tissue (as in FIG. 16a, b), i.e. of the amplitude and wavelength of the shear waves.

Representative parameters of the in vivo fractional MRE on biceps, liver and IVS are listed in FIG. 17. With q=0.6, 0.33 and 0.1, the MRE motion encoding of biceps to heart becomes more and more "fractional". The proposed oscillation frequencies perhaps are not always possible, since they depend on $TR_{min}$, which in turn is determined by the image resolution. The PNR was calculated with the above-described equation and with the following parameters: $TR_{min}$: 3.5 ms, $SNR_0$=11, $|G_{ME}|$=35 mT/m; $|u_0|$=100 μm; muscle: $T_2^*$=17 ms, μ=5000 Pa, η=2 Pas; liver: $T_2^*$=9 ms, μ=2000 Pa, η=4 Pas.

The parameter μ combines the elastic modules determined in the above-described measurements for liver and muscle or has been taken from the literature (Kanai H. Propagation of spontaneously actuated pulsive vibration in human heart wall and in vivo viscoelasticity estimation. IEEE Trans Ultrason Ferroelectr Freq Control 2005; 52(11):1931-1942 (ultrasound) and Wen H, Bennett E, Epstein N, Plehn J. Magnetic resonance imaging assessment of myocardial elastic modulus and viscosity using displacement imaging and phase-contrast velocity mapping. Magn Reson Med 2005; 54(3):538-548 (MRI)).

(*) The total scan time is an estimate for planar MRE with a recording of 8 θ shifts and a matrix size of 128 (biceps, liver) and 64 (heart), respectively. (**) In the case of the heart, an individual scan generates two images Δφ(θ) and Δφ(θ+90°) as compared to 2Δφ=A−C+i(B−D), as described above.

| List of Reference Numerals | |
|---|---|
| 1 | patient |
| 11 | head |
| 13 | section |
| 14 | bright spot |
| 2 | tomograph |
| 21 | magnet |
| 211 | receiving aperture |
| 212 | superconducting coil |
| 213 | coil |
| 214 | main excitation coil |
| 3 | motion source |
| 31 | loudspeaker |
| 311 | joint |
| 3111 | joint head |
| 3112 | joint portion |
| 312 | loudspeaker membrane |
| 315 | electrical connections |
| 316 | stabilizing sleeve |
| 32 | supporting rack |
| 320 | adhesive |
| 321 | plastic supporting plate |
| 322 | threaded pin |
| 323 | threaded pin |
| 33 | housing |
| 34 | rollers |
| 35 | loudspeaker module |
| 357 | contact point |
| 30 | active loudspeaker |
| 301 | active loudspeaker membrane |
| 4 | tube |
| 41 | end |
| 441 | positive fit |
| 442 | screw connection |
| 44 | end piece |
| 400 | rod |
| 403 | end |
| 45 | end piece |
| 453 | joint head |
| 454 | plastic tube |
| 455 | window |
| 456 | roller |
| 46 | end piece |
| 461 | ball head |
| 462 | excitation rod |
| 463 | ball joint |
| 464 | positioning rack |
| 465 | transmission head |
| 466 | clamping screw |
| 467 | bearing unit |
| 468 | horizontal attachment |
| 469 | spacer rod |
| 470 | base plate |
| 5 | function generator |
| 6 | amplifier |
| 7 | MRT control |

The invention claimed is:

1. A device for generating mechanical oscillations in an examination object using magnetic resonance elastography (MRE), comprising
   a membrane which can be set in periodic motions, and
   a transmission element for transmitting periodic motions of the membrane to the examination object,
   wherein the membrane is connected with the transmission element via mounting means and configured to pass on periodic motions of the membrane to the transmission element via the mounting means in order to generate mechanical oscillations in the examination object.

2. The device according to claim 1 wherein a surface of the membrane is connected with the transmission element.

3. The device according to claim 1, wherein the membrane is adhesively connected with the transmission element.

4. The device according to claim 3, wherein the adhesive connection is effected by means of adhesive.

5. The device according to claim 1, wherein the membrane is positively connected with the transmission element.

6. The device according to claim 1, wherein the mounting means comprise a supporting plate centrally attached to the membrane by means of an adhesive, which is connected with the transmission element.

7. The device according to claim 6, wherein that the mounting means include elements for making a screw or rivet connection between the transmission element and the membrane.

8. The device according to claim 1, wherein a tubular or rod-shaped transmission element.

9. The device according to claim 8, wherein that the membrane is connected with an end of the tubular or rod-shaped transmission element.

10. The device according to claim 9, wherein the end of the transmission element is connected with a central portion of the membrane.

11. The device according to claim 1, wherein the membrane includes a centrally arranged stabilizing sleeve for power transmission.

12. The device according to claim 1, wherein the transmission element is connected with the membrane via a joint.

13. The device according to claim 1, wherein the transmission element is rigid.

14. The device according to claim 1, wherein the transmission element is flexible.

15. The device according to claim 1, wherein that the transmission element comprises a tube filled with a liquid.

16. The device according to claim 1, wherein the membrane is a loudspeaker membrane.

17. The device according to claim 1, wherein beside the membrane (passive membrane) connected with the transmission element a further membrane, an active membrane, is arranged, by whose motions the membrane connected with the transmission element can be set in motion.

18. The device according to claim 17, wherein between the two membranes an air-filled cavity is arranged, via which motions of the active membrane are transmitted to the passive membrane.

19. The device according to claim 1, wherein that on its side facing the examination object, the transmission element includes a tubular or rod-shaped excitation element extending at an angle with respect to its main direction of extension.

20. The device of claim 1, further comprising a step motor connected to said transmission element for generating said periodic motions.

21. The device according to claim 20, wherein the step motor is coupled with the transmission element via an eccentric disk such that the periodic motion of the step motor effects a periodic reciprocating motion of the transmission element.

22. An MRE means which includes a device according to claim 1.

* * * * *